(12) United States Patent
Altschuler

(10) Patent No.: US 10,271,938 B2
(45) Date of Patent: Apr. 30, 2019

(54) MULTI-PHASIC SOLID IMPLANTS FOR TISSUE REPAIR

(71) Applicant: CARTIHEAL (2009) LTD, Kfar Saba (IL)

(72) Inventor: Nir Altschuler, Zur Yitzhak (IL)

(73) Assignee: Cartiheal (2009) LTD, Kfar Saba (IL)

( * ) Notice: Subject to any disclaimer, the term of this patent is extended or adjusted under 35 U.S.C. 154(b) by 339 days.

(21) Appl. No.: 14/390,163

(22) PCT Filed: Apr. 4, 2013

(86) PCT No.: PCT/IL2013/050312
§ 371 (c)(1),
(2) Date: Jan. 30, 2015

(87) PCT Pub. No.: WO2013/150537
PCT Pub. Date: Oct. 10, 2013

(65) Prior Publication Data
US 2015/0134065 A1 May 14, 2015

Related U.S. Application Data

(63) Continuation-in-part of application No. 14/302,184, filed on Jun. 11, 2014, now Pat. No. 10,080,818, (Continued)

(51) Int. Cl.
*A61F 2/02* (2006.01)
*A61F 2/28* (2006.01)
(Continued)

(52) U.S. Cl.
CPC .............. *A61F 2/02* (2013.01); *A61F 2/28* (2013.01); *A61F 2/30* (2013.01); *A61F 2/30756* (2013.01);
(Continued)

(58) Field of Classification Search
None
See application file for complete search history.

(56) References Cited

U.S. PATENT DOCUMENTS 6,995,013 B2 * 2/2006 Connelly ............... A61L 27/34
424/423
8,475,531 B1 * 7/2013 Maxson ............. A61F 2/30756
623/14.12
(Continued)

FOREIGN PATENT DOCUMENTS

WO WO 2010/146574 A1 12/2010
WO WO 2010/146575 A2 12/2010

OTHER PUBLICATIONS

International Search Report (ISR) for PCT/Il2013/050312; I.A. fd dated Apr. 4, 2013, dated Jul. 12, 2013 from the European Patent Office, Rijswijk, Netherlands.
(Continued)

*Primary Examiner* — Carlos A Azpuru
*Assistant Examiner* — Casey S Hagopian
(74) *Attorney, Agent, or Firm* — Sterne, Kessler, Goldstein & Fox P.L.L.C.

(57) ABSTRACT

This invention provides aragonite- and calcite-based solid substrates for the repair, regeneration, enhancement of formation or a combination thereof of cartilage and/or bone, which solid substrates comprise or are made to ultimately comprise three phases, wherein each phase differs in terms of its chemical content, or structure, kits comprising the same, and methods of use thereof.

17 Claims, 2 Drawing Sheets

Related U.S. Application Data which is a continuation of application No. 13/378,474, filed as application No. PCT/IL2010/000410 on May 23, 2010, now Pat. No. 8,790,681.

(60) Provisional application No. 61/773,219, filed on Mar. 6, 2013, provisional application No. 61/773,228, filed on Mar. 6, 2013, provisional application No. 61/764,467, filed on Feb. 13, 2013, provisional application No. 61/763,985, filed on Feb. 13, 2013, provisional application No. 61/764,496, filed on Feb. 13, 2013, provisional application No. 61/763,981, filed on Feb. 13, 2013, provisional application No. 61/620,512, filed on Apr. 5, 2012, provisional application No. 61/252,800, filed on Oct. 19, 2009, provisional application No. 61/187,081, filed on Jun. 15, 2009.

(51) Int. Cl.
| | |
|---|---|
| A61F 2/30 | (2006.01) |
| A61L 27/14 | (2006.01) |
| A61L 27/18 | (2006.01) |
| A61L 27/20 | (2006.01) |
| A61L 27/22 | (2006.01) |
| A61L 27/24 | (2006.01) |
| A61L 27/34 | (2006.01) |
| A61L 27/36 | (2006.01) |
| A61L 27/38 | (2006.01) |
| A61L 27/46 | (2006.01) |
| A61L 27/52 | (2006.01) |
| A61L 27/56 | (2006.01) |

(52) U.S. Cl.
CPC ......... *A61F 2/30767* (2013.01); *A61L 27/14* (2013.01); *A61L 27/18* (2013.01); *A61L 27/20* (2013.01); *A61L 27/225* (2013.01); *A61L 27/227* (2013.01); *A61L 27/24* (2013.01); *A61L 27/34* (2013.01); *A61L 27/36* (2013.01); *A61L 27/3604* (2013.01); *A61L 27/365* (2013.01); *A61L 27/3654* (2013.01); *A61L 27/3804* (2013.01); *A61L 27/3817* (2013.01); *A61L 27/3834* (2013.01); *A61L 27/46* (2013.01); *A61L 27/52* (2013.01); *A61L 27/56* (2013.01); *A61F 2002/30016* (2013.01); *A61F 2002/30075* (2013.01); *A61F 2002/3092* (2013.01); *A61F 2210/008* (2013.01); *A61F 2210/0076* (2013.01); *A61F 2310/00341* (2013.01); *A61F 2310/00371* (2013.01); *A61L 2430/02* (2013.01); *A61L 2430/06* (2013.01)

(56) References Cited

U.S. PATENT DOCUMENTS

| | | | |
|---|---|---|---|
| 8,790,681 B2 | 7/2014 | Altschuler et al. | |
| 8,802,115 B2 | 8/2014 | Altschuler et al. | |
| 8,808,725 B2 | 8/2014 | Altschuler et al. | |
| 2003/0114936 A1* | 6/2003 | Sherwood | A61F 2/28 623/23.58 |
| 2011/0200563 A1 | 8/2011 | Vago | |
| 2011/0256228 A1 | 10/2011 | Altschuler et al. | |
| 2012/0177702 A1 | 7/2012 | Altschuler et al. | |
| 2012/0189669 A1 | 7/2012 | Altschuler et al. | |

OTHER PUBLICATIONS

International Preliminary Report on Patentability (Chapter I of the Patent Cooperation Treaty) including the Written Opinion of the International Searching Authority for PCT/Il2013/050312; I.A. fd dated Apr. 4, 2013, dated Oct. 7, 2014, from the International Bureau of WIPO, Genera, Switzerland.

Gravel, M et al., "Responses of mesenchymal stem cell to chitosan-coralline composites microstructured using coralline as gas forming agent," Biomaterials, Mar. 2006, 27(9): 1899-1906, Elsevier Science Publishers, Barking, GB.

Excerpted file history, U.S. Appl. No. 13/378,474 (now U.S. Pat. No. 8,790,681), including prosecution documents dated Dec. 15, 2011-Jul. 9, 2014.

Excerpted file history, U.S. Appl. No. 13/130,272 (now U.S. Pat. No. 8,808,725), including prosecution documents dated May 19, 2011-Jul. 30, 2014.

\* cited by examiner

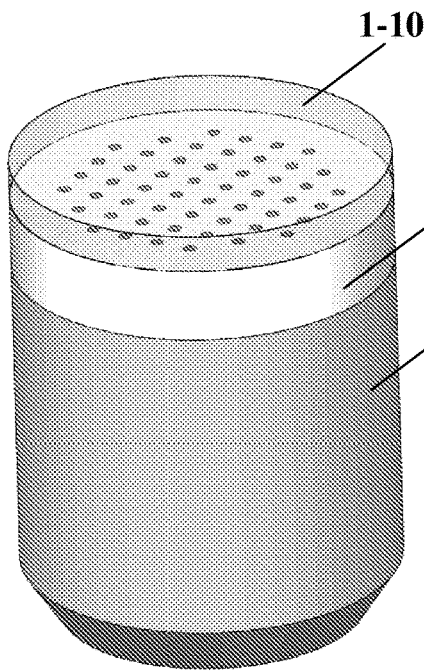
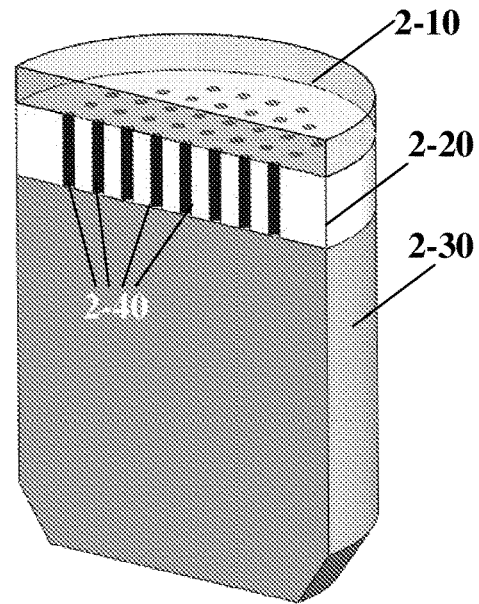
Figure 1  Figure 2
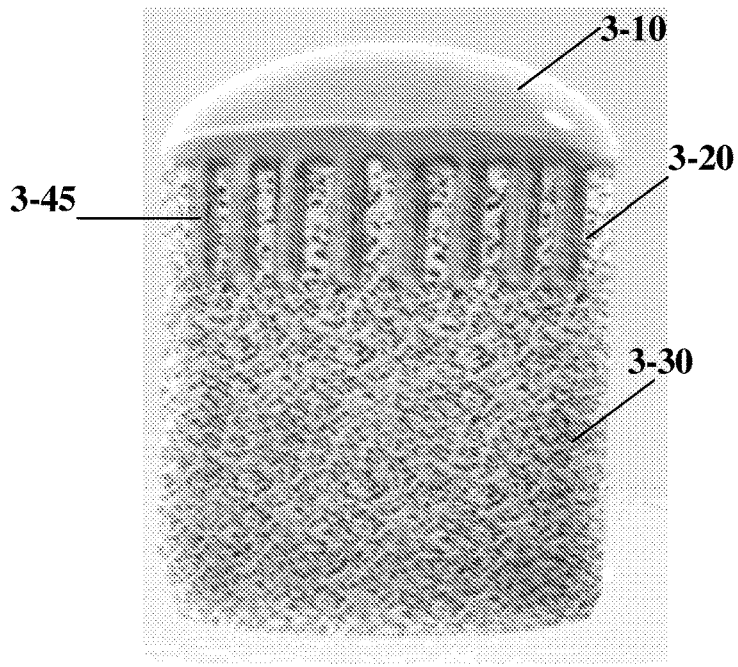
Figure 3

MULTI-PHASIC SOLID IMPLANTS FOR TISSUE REPAIR

CROSS REFERENCE TO RELATED APPLICATIONS

This application claims the benefit of U.S. Provisional Application Ser. No. 61/620,512 filed Apr. 5, 2012, U.S. Provisional Application Ser. No. 61/763,981 filed Feb. 13, 2013, U.S. Provisional Application Ser. No. 61/763,985 filed Feb. 13, 2013, U.S. Provisional Application Ser. No. 61/764,467 filed Feb. 13, 2013, and U.S. Provisional Application Ser. No. 61/764,496 filed Feb. 13, 2013, all of which are hereby incorporated by reference herein in their entirety.

BACKGROUND OF THE INVENTION

Tissue growth, regeneration and repair are often necessary to restore function and reconstruct the morphology of the tissue, for example, as a result of exposure to trauma, neoplasia, abnormal tissue growth, aging, and others.

Synthetic materials have also used as a substrate for promoting ex-vivo tissue assembly and repair, and similarly for restoring and reconstructing different tissues, for example for bone, for many years, with mixed success. Another possibility is autologous tissue grafting, although the supply of autologous tissue is limited and its collection may be painful, with the risk of infection, hemorrhage, cosmetic disability, nerve damage, and loss of function. In addition, significant morbidity is associated with autograft harvest sites. These problems may be overcome by engineering tissue using solid substrates made of synthetic or natural biomaterials that promote the adhesion, migration, proliferation, and differentiation of stem cells, for example, mesenchymal stem cells (MSCs).

Many diseases and conditions whose treatment is sought would benefit from the ability to promote cell and tissue growth in a site-specific manner, promoting growth and incorporation of new tissue within a damaged or diseased site.

In bone and cartilage applications, the immediate microenvironment and the three-dimensional (3D) organization are important factors in differentiation in general and particularly in chondrogenic and osteogenic differentiation.

Some bone tissue engineering scaffolds consists of natural polymers, such as collagen, alginate, hyaluronic acid, and chitosan. Natural materials offer the advantages of specific cell interaction, easy seeding of cells because of their hydrophilic interactions, low toxicity and low chronic inflammatory response. However, these scaffolds often are mechanically unstable and do not readily contribute to the creation of tissue structures with a specific predefined shape for transplantation. To obtain mechanical strength, chemical modification is required, which may lead to toxicity.

Defects and degeneration of the articular cartilage surfaces of joints causes pain and stiffness. Damage to cartilage which protects joints can result from either physical injury as a result of trauma, sports or repetitive stresses (e.g., osteochondral fracture, secondary damage due to cruciate ligament injury) or from disease (e.g. osteoarthritis, rheumatoid arthritis, aseptic necrosis, osteochondritis dissecans).

Osteoarthritis (OA) results from general wear and tear of joints, most notably hip and knee joints. Osteoarthritis is common in the elderly but, in fact, by age 40 most individuals have some osteoarthitic changes in their weight bearing joints. Another emerging trend increasing the prevalence of osteoarthritis is the rise in obesity. The CDC estimates that 30% of American adults (or 60 million people) are obese. Obese adults are 4 times more likely to develop knee OA than normal weight adults Rheumatoid arthritis is an inflammatory condition which results in the destruction of cartilage. It is thought to be, at least in part, an autoimmune disease with sufferers having a genetic predisposition to the disease.

Orthopedic prevention and repair of damaged joints is a significant burden on the medical profession both in terms of expense and time spent treating patients. In part, this is because cartilage does not possess the capacity for self-repair. Attempts to re-grow hyaline cartilage for repair of cartilage defects remain unsuccessful. Orthopedic surgery is available in order to repair defects and prevent articular damage in an effort to forestall serious degenerative changes in a joint. The use of surgical techniques often requires the removal and donation of healthy tissue to replace the damaged or diseased tissue. Techniques utilizing donated tissue from autografts, allografts, or xenografts are wholly unsatisfactory as autografts add additional trauma to a subject and allografts and xenografts are limited by immunological reactivity to the host subject and possible transfer of infective agents. Surgical attempts to utilize materials other than human or animal tissue for cartilage regeneration have been unsuccessful.

An ideal material which restores tissue function and facilitates reconstruction of the morphology of such tissue is as yet, lacking.

SUMMARY OF THE INVENTION

In some embodiments, this invention provides a solid substrate for tissue repair, said solid substrate consisting essentially of three phases wherein:
  a first phase of said three phases comprises a first biocompatible polymer, which biopolymer layer is characterized by being comprised of an elastic material which is substantially less rigid in structure than that of said second and third phases of said three phases;
  a second phase of said three phases comprises a marine organism skeletal derivative-based solid substrate comprising a second biocompatible polymer and said second phase further comprises a series of hollows along a longitudinal axis in said second phase, wherein said biocompatible polymer is substantially located within said series of hollows; and
  a third phase of said three phases comprises a marine organism skeletal derivative-based solid substrate, optionally comprising a series of hollows along a longitudinal axis in said third phase.

In some embodiments, according to this aspect, the first biocompatible polymer is in the form of a hydrogel.

In some embodiments, said first phase is elastic following wetting in situ.

In some embodiments, according to this aspect, the first or second biocompatible polymer or a combination thereof comprises collagen, cross-linked collagen, chitosan, elastin, silk, aliginate, fibrin, platelet rich plasma, a glycosaminoglycan, or combinations thereof. In some embodiments, according to this aspect, the glycosaminoglycan is hyaluronic acid, sodium hyaluronate, or a cross linked hyaluronic acid or a combination thereof. In some embodiments, according to this aspect, the alginate may comprise calcium alginate, cross linked calcium alginate or a combination thereof. In some embodiments, according to this aspect, the chitosan may comprise cross linked chitosan.

In some embodiments, a third, fourth, or any number of additional biocompatible polymers may be incorporated within the solid substrates of this invention.

In some embodiments, according to this aspect, the solid substrate further comprises at least one cell population suspended therein or seeded thereon. In some embodiments, according to this aspect, the at least one cell population is a population of chondrocytes or progenitor cells therefor.

In some embodiments, according to this aspect, the coral or coral derivative is aragonite, calcite, mixtures thereof, or other polymorphs of the same. In some embodiments, the solid substrate is isolated from a *Porites* species, a *Goniopora*, a *Millepora* species or an *Acropora* species.

In some embodiments, according to this aspect, the first or second biocompatible polymer further comprises a cytokine, a growth factor, a chelator, a cell population, a therapeutic compound, a drug, or any combination thereof. In some embodiments, according to this aspect, the therapeutic compound or drug comprises an anti-inflammatory compound, an anti-infective compound, a pro-angiogenic factor or a combination thereof.

In some embodiments, according to this aspect, the said first and said second phase are designated for insertion into a region which is proximal to cartilage and said third phase is designated for insertion into a region which is proximal to subchondral bone.

In some embodiments, the marine organism skeletal derivative is characterized by a specific fluid uptake capacity value of at least 75%, which specific fluid uptake capacity value is determined by establishing a spontaneous fluid uptake value divided by a total fluid uptake value.

In some embodiments, the marine organism skeletal derivative is characterized by having a contact angle value of less than 60 degrees, when in contact with a fluid.

In some embodiments, according to these aspects, the fluid is a protein-containing, salt-containing or carbohydrate containing solution. In some embodiments, the fluid is a biologic fluid. In some embodiments, the biologic fluid is autologous with respect to a cell or tissue of a subject when said solid substrate is contacted with a cell or tissue of said subject. In some embodiments, the fluid is water.

In some embodiments, according to this aspect, the invention provides a method of inducing or enhancing repair, regeneration or enhancement of formation of cartilage, bone or a combination thereof, said method comprising implanting in a subject, a solid substrate as herein described (and in accordance with any permutation thus described) within a site in need of repair, regeneration or enhancement of formation of cartilage, bone or a combination thereof.

In some embodiments, the method comprises rendering the first phase more elastic following wetting of the first phase as a consequence of or during the implantation of the solid substrate.

In some embodiments, the invention provides a method of inducing or enhancing repair, regeneration or enhancement of formation of cartilage, bone or a combination thereof, said method comprising:
implanting within a site in need of repair, regeneration or enhancement of formation of cartilage, bone or a combination thereof in a subject, a solid substrate comprising:
a first phase comprising a marine organism skeletal derivative-based solid substrate comprising a first biocompatible polymer and said first phase further comprises a series of hollows along a longitudinal axis in said first phase, wherein said first biocompatible polymer is substantially located within said series of hollows; and
a second phase comprising a marine organism skeletal derivative-based solid substrate, optionally comprising a series of hollows along a longitudinal axis in said second phase;
whereby said implanting places said solid substrate below an upper limit of said site in need of repair, and
applying a second biocompatible polymer to a region above said first phase to be slightly less than, be flush with or be slightly above an upper limit of said site in need of repair.

In some embodiments, the solid substrate comprises a third phase created when said second biocompatible polymer is applied, which second biocompatible polymer is of the same material as said first biocompatible polymer, and wherein said first phase is assembled, by applying said first biocompatible polymer at the same time as applying said second biocompatible polymer.

In some embodiments, the first and third phases are assembled during or following the implantation of the solid substrate.

In some embodiments, the method comprises exposing a site of cartilage repair, and optionally exposing bone tissue located proximally to the site of cartilage repair in the subject prior to implanting the solid substrate.

In some embodiments, this invention provides for the use of a solid substrate as herein described (in any embodied permutation as described herein) for inducing or enhancing repair, regeneration or enhancement of formation of cartilage, bone or a combination thereof.

All publications, patents, and patent applications mentioned herein are hereby incorporated by reference in their entirety as if each individual publication or patent was specifically and individually indicated to be incorporated by reference. In case of a conflict between the specification and an incorporated reference, the specification shall control. Where number ranges are given in this document, endpoints are included within the range. Furthermore, it is to be understood that unless otherwise indicated or otherwise evident from the context and understanding of one of ordinary skill in the art, values that are expressed as ranges can assume any specific value or sub-range within the stated ranges, optionally including or excluding either or both endpoints, in different embodiments of the invention, to the tenth of the unit of the lower limit of the range, unless the context clearly dictates otherwise. Where a percentage is recited in reference to a value that intrinsically has units that are whole numbers, any resulting fraction may be rounded to the nearest whole number.

BRIEF DESCRIPTION OF THE DRAWINGS

FIG. 1 schematically depicts an embodiment of a solid substrate/implants of this invention. According to this aspect, a first phase 1-10 is located most apically and comprises a first biocompatible polymer, and a second phase 1-20 comprises aragonite throughout which are a series of holes or voids along a longitudinal axis which are impregnated or accumulated therewithin is a second biocompatible polymer, such as hyaluronic acid and a third phase 1-30 comprising only aragonite.

FIG. 2 schematically depicts the embodied solid substrate of FIG. 1, cut along a longitudinal axis, in order to better view the series of voids 2-40 along the longitudinal axis.

FIG. 3 schematically depicts the embodied scaffold of FIG. 1, with the porosity of the aragonite-containing elements emphasized, as well as depicting the presence of a second biocompatible polymer 3-45 within the voids in the second phase 3-20. The first 3-10 and third phases 3-30, respectively, are depicted, as well.

DETAILED DESCRIPTION OF THE PRESENT INVENTION

Figure 4A:
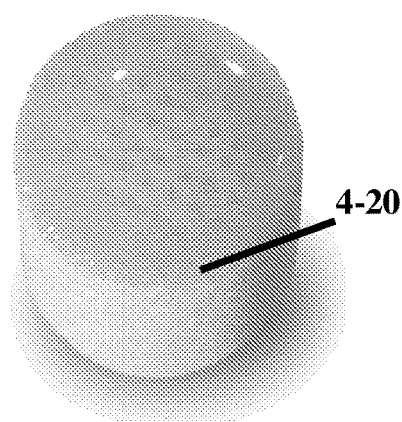
FIGS. 4A and 4B provide photographs of an embodied scaffold of this invention, showing top/front and side views. The first 4-10 and third phases 4-30, (FIG. 4B), respectively, are evident, with the second phase shown 4-20 (FIG. 4A) more clearly depicted in the depiction in FIG. 3.

This invention provides, inter alia, solid substrates, and methods of use thereof for repair and/or formation of cartilage and/or bone tissue in a subject. This invention further provides kits for repair and/or formation of cartilage and/or bone tissue in a subject.

This invention provides, inter alia, optimized solid substrates for promoting cell or tissue growth or restored function and processes for producing the same.

Coral, which is comprised of $CaCO_3$ in the crystalline form of aragonite or calcite has the advantage of supporting fast cellular invasion, adherence, proliferation and differentiation of mesenchymal stem cells into cartilage and/or bone tissue.

Three-dimensional (3-D) solid substrates attract mesenchymal stem cells from surrounding or proximally located tissue and promote blood vessel formation to a site of cartilage repair. Such solid substrates can be used for regeneration, repair and enhancement of formation of cartilage and/or bone in a subject for the treatment of full-thickness cartilage defects, partial thickness cartilage defects and/or osteochondral defects.

The solid substrates of this invention will comprise a marine organism skeletal derivative-based material.

In some embodiments, the term "marine organism skeletal derivative-based material" refers to a solid piece or ground material derived from a marine organism, and from a skeletal component of the organism, such as an exoskeleton of the same.

In some embodiments, the term "marine organism skeletal derivative-based material" refers to a coralline-based material. Coral, which is comprised of $CaCO_3$ in the crystalline form of aragonite or calcite has been shown to possess the advantage of supporting fast cellular invasion, adherence and proliferation. Coral has been shown to be an effective substrate for facilitation of the adherence, proliferation and differentiation of mesenchymal stem cells, and ultimate incorporation into cartilage and/or bone tissue. Coral has also been shown to serve as an excellent substrate for promoting adherence and proliferation of a number of other cell types, serving as an excellent support for cell and tissue growth.

The terms "coral" and "aragonite" and "calcite" may be used interchangeably herein.

In some embodiments, the term "marine organism skeletal derivative-based material" refers to a coral or coral derivative. In some embodiments, the term "marine organism skeletal derivative-based material" refers to barnacle or mollusk-derived skeletal material, and in some embodiments, inclusion of nacre is contemplated.

In some embodiments, the solid substrate contains ground particles derived from coral, suspended in a biocompatible matrix. In some embodiments, the biocompatible matrix is a hydrogel.

In some embodiments, reference to an "implant" or "plug" or "solid substrate", as used herein refers to any embodiment or combined embodiments as herein described with regard to the solid substrates and to be considered as being included in the described aspect of this invention. For example, reference to a "solid substrate" as used herein, is to be understood to refer to any embodiment of a solid substrate as described herein being applicable for the indicated purpose or containing the indicated attribute, etc.

In one embodiment, "solid substrate" refers to a shaped platform used for cell and/or tissue repair and/or restored function, wherein the shaped platform provides a site for such repair and/or restored function. In one embodiment, the solid substrate is a temporary platform. In one embodiment, "temporary platform" refers to a natural degradation of a coral of this invention that occurs over time during such repair, wherein the natural fully or partially degradation of the coral may results in a change of solid substrate shape over time and/or change in solid substrate size over time.

It will be appreciated that different species of coral vary in terms of their average pore diameter and pore volume and the invention contemplates use of any such coral as a starting material for the preparation of the solid substrates as herein described. As used herein, the term "pore volume" refers to volume or open spaces inside the porous scaffolding of this invention. Pore volume is determined by any means known in the art. Porosity can be calculated by standard methods, an example of which is provided further hereinbelow, see for example, Karageorgiou V, Kaplan D. (2005) "Porosity of 3D biomaterial scaffolds and osteogenesis" Biomaterials.; 26(27):5474-91, which is hereby incorporated by reference in its entirety.

It will be appreciated that the term "coral" will refer to a starting material from which aragonite, calcium carbonate, calcite, or hydroxyapatite etc. may be isolated.

The coralline-based or calcite-based, etc., solid substrates of this invention may also be used for regeneration, repair and enhancement of formation of bone in a subject, for the treatment of a bone condition, disease or disorder.

This invention provides the unexpected application of the described solid substrates for use in a three-phase arrangement, either inserted as a tri-phasic scaffolding material, or inserted as a bi-phasic solid substrate, whereby the third phase is assembled in situ. Such solid substrates are uniquely and superiorly useful in cartilage and/or bone regeneration, repair and enhancement of formation and moreover, that such solid substrates can be prepared and inserted specifically and optimally within cartilage and/or bone in a subject in need thereof, for methods of cartilage and/or bone regeneration, repair and enhancement of formation.

In particular, this invention provides the unexpected application that cartilage and/or bone regeneration, repair and enhancement of formation is optimal when the coral scaffolding consists essentially of three phases wherein:

a first phase of said three phases comprised substantially of a first biocompatible polymer, which first phase is characterized by being comprised of an elastic material, and which material is substantially less rigid in structure than that of said second and third phases of said three phases;

a second phase of said three phases comprises s marine organism skeletal derivative-based solid substrate comprising a second biocompatible polymer and said second phase further comprises a series of hollows along a longitudinal axis in said second phase, wherein said biocompatible polymer is substantially located within said series of hollows; and a third phase of said three phases comprises a marine organism skeletal derivative-based solid substrate, optionally comprising a series of hollows along a longitudinal axis in said third phase.

In particular, this invention provides the unexpected advantage in terms of greater incorporation of the solid substrate within the newly developed cartilage, and reduced inflammation, when the solid substrates are structured such as those herein described.

Another advantage to the solid substrates according to this aspect, is the presence of pre-drilled channels or longitudinally placed holes within the phase containing the biocompatible polymer such as hyaluronic acid, which holes are impregnated with the biocompatible polymer such as hylauronic acid and serve as a reservoirs for the biocompatible polymer such as hyaluronic acid in a phase located within a region in need of cartilage repair. Localization of the biocompatible polymer such as hyaluronic acid allows for greater direction of migrating progenitor cells throughout the phase of this solid substrate to stimulate cartilage regeneration and repair. In some embodiments, the channels comprising concentrated biocompatible polymer such as hyaluronic acid within the voids along the longitudinal axis of the phase of the solid substrate provide a chemotactic guide for recruited cells involved in chondrogenesis, and/or in some embodiments, influence local recruitment and differentiation of the chondrogenic population of cells migrating thereto. In some embodiments, the channels comprising concentrated biocompatible polymer such as hyaluronic acid within the voids along the longitudinal axis of the phase of the solid substrate contribute to cartilage matrix homeostasis.

Unexpectedly, it was found that apical placement of a phase consisting essentially of the biocompatible polymer, and positioning of the same within the site of repair, or positioning the same slightly under, flush or slightly over the upper limit of the site of defect provides for greater incorporation within the defect site and reduced inflammation associated therewith.

According to this aspect, the porosity and greater rigidity of the third phase as compared to the first is more suited for insertion within bone and provides a support, for the repair of osteochondral defects. The solid substrates of this invention are therefore, in some embodiments, ideally suited for incorporation within a defect site that spans two different types of tissue, i.e. bone and cartilage.

In some embodiments, according to this aspect, the first phase has a height of between 0.1-4 mm, or in some embodiments, 0.1-3 mm, or in some embodiments, 0.1-1 mm, or in some embodiments, 0.5-3 mm, or in some embodiments, 0.5-4 mm, or in some embodiments, 0.5-2 mm, or in some embodiments, 1-2 mm, or in some embodiments, 1-3 mm, or in some embodiments, 1-4 mm, or in some embodiments, 0.01-0.5 mm, or in some embodiments, 0.03-0.1 mm, or in some embodiments, 0.05-0.15 mm.

In some embodiments, the first and second biocompatible polymer, are hydrophilic, and when synovial fluid comes into contact therewith at the apical layer above the solid substrate, or when saline comes into contact therewith during the implantation procedure, the implant absorbs the fluid and reverts to a hydrogel, as opposed to the pre-implantation dehydrated/dessicated state. This reversion provides mechanical protection at the site of implantation, in some embodiments.

In some embodiments, the exterior layer, when "reconstituted" as described following implantation, may elute from the solid substrate into the surrounding site and thereby participate in the stimulation or enhancement of repair at the site, including inter alia, serving as a chemoattractant for cells involved in the repair process.

In some embodiments, a bi-phasic implant consisting of the second and third phases as herein described is inserted within a defect site and the first phase is applied apically above the implanted scaffolding, creating or constituting in situ assembly of the three-phase implant.

It will be appreciated by the artisan, that reference to the terms "first", "second" and "third", in particular, as relating to the described phases within the implants of this invention, are to designate the presence of the one, two or three elements, and are to be defined by their constituents.

Thus, in one embodiment, this invention provides a method of inducing or enhancing repair, regeneration or enhancement of formation of cartilage, bone or a combination thereof, said method comprising implanting in a subject, a solid substrate this invention (including any embodiment with respect thereto as herein described), within a site in need of repair, regeneration or enhancement of formation of cartilage, bone or a combination thereof. In some embodiments, the method comprises rendering said first phase more elastic following wetting of said first phase as a consequence of or during said implanting.

Thus, in another embodiment, this invention provides a method of inducing or enhancing repair, regeneration or enhancement of formation of cartilage, bone or a combination thereof, said method comprising implanting within a site in need of repair, regeneration or enhancement of formation of cartilage, bone or a combination thereof in a subject, a solid substrate comprising:

a first phase comprising a marine organism skeletal derivative-based solid substrate comprising a first biocompatible polymer and said first phase further comprises a series of hollows along a longitudinal axis in said first phase, wherein said first biocompatible polymer is substantially located within said series of hollows; and; and a second phase comprising a marine organism skeletal derivative-based solid substrate, optionally comprising a series of hollows along a longitudinal axis in said second phase;

whereby said implanting places said solid substrate within said site in need of repair, and applying a second biocompatible polymer to a region above said first phase to be slightly less than, be flush with or be slightly above an upper limit of said site in need of repair.

In some embodiments, the solid substrate comprises a third phase created when said second biocompatible polymer is applied, which second biocompatible polymer is of the same material as said first biocompatible polymer, and wherein said first phase is assembled, by applying said first biocompatible polymer at the same time as applying said second biocompatible polymer. In some embodiments, the first and third phases are assembled during or following implantation.

In some embodiments, the phase comprising a biocompatible polymer, and further comprising a series of hollows along a longitudinal axis in said phase, wherein the biocompatible polymer is substantially located within the series of hollows, is typically referred to herein as the second phase. Such second phase will comprise a series of longitudinal holes, which longitudinal holes may range from 15-60 holes placed throughout the phase along a longitudinal axis of the implant according to this aspect. In some embodiments, the holes or enlarged voids will have a diameter ranging from about 250-450 µm. In some embodiments, the holes or enlarged voids will have a diameter ranging from about 125-650 µm, or in some embodiments, ranging from about 175-550 µm.

According to this aspect, and in some embodiments, the series of holes or voids may be incorporated by physical manipulation of the implant, for example, and in some embodiments, solid aragonite or calcite may be isolated, cleaned and otherwise prepared as described herein, and a drill may be used to create the series of holes/voids as herein described. In some embodiments, other means, such as selective dissolution of the scaffolding material may be accomplished, where the selective dissolution along a longitudinal axis is accomplished by methods known in the art, including those described and exemplified herein.

According to this aspect, the solid substrates further comprise a phase containing a marine organism skeletal derivative-based solid substrate, such as, for example, solid coral or biolattice, which has not been further modified to alter the porosity of the phase, or in some embodiments, may be altered as described further hereinunder to specifically alter the pore volume or average pore diameter in the phase, whereby such modifications are substantially uniform throughout the phase. Such phase is typically referred to herein as the third phase.

Incorporation of a biocompatible polymer such as hyaluronic acid in the first and second phase of the implant or in both phases, may be accomplished via any means, including pressure-driven application, for example, via application under vacuum, centrifugal force or mechanical pressure. In some embodiments, gravitational force is sufficient to allow appropriate and relatively homogenous penetration of the hyaluronic acid to a desired depth of the implant, creating the first phase as herein described. According to this aspect, in one embodiment, visual inspection of the implant, for example using the staining with Fast Green/Safranin O, demonstrates uniform distribution of the hyaluronic acid through the phase and to a desired depth as a function of the time and conditions of application.

According to this aspect, and in some embodiments, when applying the solid substrates to a site of bone and/or cartilage repair, or in some embodiments, to a defect site where both bone and cartilage are affected and in need of repair and/or regeneration, the skilled artisan will appreciate that the third phase of the solid substrate is inserted within the bone defect site whereas the first and second phases are inserted within the cartilage defect site and are ensured to be flush with or slightly below the upper limit of the defect site.

In some embodiments, such solid substrates may be administered to a subject with a bone defect in need of repair, wherein access to the bone defect results in the creation of a defect in the overlying cartilage, and the solid substrates of this invention allow for the healing of both affected tissues. In other embodiments, such solid substrates may be administered to a subject with a cartilage defect in need of repair, wherein optimal insertion of the solid substrate for stimulation of cartilage repair necessitates anchoring of the solid substrate in the underlying bone, for example, by creating a minimal void in the underlying bone for insertion of the solid substrate, and once inserted, the solid substrate facilitates repair of both the overlying cartilage and underlying bone.

In other embodiments, such solid substrates may be administered to a subject with an osteochondral defect, where both bone and cartilage tissue are in need of repair as part of the pathogenesis of the disorder. The solid substrates according to this aspect are, in some embodiments, particularly suited for such applications.

This invention also provides for the unexpected application that cartilage and/or bone regeneration, repair and enhancement of formation is optimal when the coral scaffolding comprises at least two phases, which phases comprise voids, and vary in terms of the average diameter of the voids within each phase, and/or that cartilage and/or bone regeneration, repair and enhancement of formation is optimal when the coral scaffolding comprises at least two phases, which phases vary in terms of their respective pore volumes (porosity).

It will be appreciated that the term "coral" will refer to a starting material from which aragonite and/or calcite may be isolated.

In one embodiment, the present invention provides a solid substrate for inducing or enhancing cartilage or bone regeneration, repair, enhancement of formation, or a combination thereof, which solid substrate consists of a solid form of aragonite or calcite and further comprises:
　　at least a first phase, comprising voids having an average diameter ranging from about 60-160 µm; and
　　at least a second phase, comprising voids having an average diameter ranging from about 170-850 µm.

It will be appreciated that according to this aspect, the term "first phase" and "second phase" do not apply to a particular order with respect to insertion of the phase within an osteochondral defect, and either the first phase or the second phase may be oriented to be proximal to cartilage within a repair site, as opposed to the prior embodiment of a solid substrate as described hereinabove, wherein the first phase is inserted proximal to a site of cartilage repair. According to this aspect, the solid substrate may be further modified to comprise both the indicated void average diameter, and either phase may further comprise a biocompatible polymer such as hyaluronic acid and a series of voids or holes along a longitudinal axis of said phase, wherein the biocompatible polymer such as hyaluronic acid is located substantially within such series of voids or holes.

In some embodiments, the term "solid form" with respect to aragonite, refers to solid aragonite harvested from coral, which aragonite is treated to remove debris, proteins and other particulate matter, however, such coral-derived materials are not hydrothermally transformed, nor ground, and resuspended.

In some embodiments, the coral for use in the preparation of the solid substrates of this invention may be processed by any means known in the art, for example, as described in PCT International Application Publication Number WO 2009/066283, PCT International Application Publication Number WO 2010/058400, PCT International Application Publication Number WO 2010/146574 and PCT International Application Publication Number WO 2010/146574, each of which is fully incorporated by reference herein, in its entirety.

In some embodiments, the coral may be processed according to a process as herein described.

In some embodiments, this invention provides a process for the purification of a coralline-based scaffolding, said process comprising the steps of:
- contacting solid aragonite of a desired size and shape with a solution comprising an oxidizing agent; and
- washing and drying said solid aragonite
- whereby one or each of said steps is conducted under applied negative pressure.

According to this aspect, and in some embodiments, the applied negative pressure ranges between about 0.2 to 0.00001 Bar, or in some embodiments, the applied negative pressure ranges between 0.4 to 0.0000001 Bar.

According to this aspect, and in some embodiments, the oxidizing agent for use in the processes of this invention may be any suitable oxidizing agent, which facilitates the removal of organic debris from coralline-based solid substrates.

In some embodiments, the oxidizing agent may include, inter alia, potassium nitrate (KNO3), hypochlorite and other hypohalite compounds, iodine and other halogens, chlorite, chlorate, perchlorate, permanganate salts, ammonium cerium(IV) nitrate, hexavalent chromium compounds, pyridinium chlorochromate (PCC), and chromate/dichromate compounds, peroxide compounds, sulfoxides, persulfuric acid, or nitric acid, acetone, ammonium peroxydisulfate, 1,4-benzoquinone, N-tert-butylbenzensulfinilmidoyl, chloride, tert-butyl hydroperoxide, tert-butyl hypochlorite, 3-chloroperoxybenzoic acid, meta-chloroperbenzoic acid, cumene hydroperoxide, dimethyl sulfoxide, hydrogen peroxide, manganese oxide, meta-chloroperbenzoic acid, N-methylmorpholine-N-oxide, methyltrioxorhenium (MTO), oxalyl chloride, N-tert-butylbenzenesulfinimidoyl chloride, oxone, oxygen, ozone, peracetic acid, periodic acid, peroxy acid, pivaldehyde, potassium permanganate, potassium peroxydisulfate, potassium peroximonosulfate, 2-propanone, sodium chlorite, sodium percarbonate, sodium periodate, styrene, trichloroisocyanuric acid (TCCA), 2,2,6, 6-tetramethylpiperidinyloxy TEMPO, tert-butyl hydroperoxide, tert-butyl hypochlorite, tetrabutylammonium peroxydisulphate, trimethylacetaldehyde. In some embodiments, the oxidizing agent is sodium hypochlorite.

According to this aspect, and in some embodiments, the process comprises conducting said contacting under mildly acidic conditions.

According to this aspect, and in some embodiments, the process comprises subjecting the solid aragonite to a temperature of at least 275° C. under applied negative pressure.

According to this aspect of the invention, the process comprises contacting the aragonite with an oxidizing agent under applied negative pressure, washing and drying the aragonite applied negative pressure, or both steps are conducted under applied negative pressure. The applied negative pressure ranges between 0.2 to 0.00001 Bar, or in some embodiments, between about 0.4 to 0.0000001 Bar, according to this aspect of the invention.

The solid substrates, kits, processes and methods of this invention make use of solid coralline forms.

The solid forms or solid substrates of this invention may be of aragonite or calcite origin.

In some embodiments, the term "solid form" with respect to calcite refers to calcite isolated from coral, which calcite is treated to remove debris, proteins and other particulate matter, however, such materials are not hydrothermically transformed, nor ground, and resuspended. In some embodiments, the "solid form" calcite refers to calcite obtained by the preparation of an aragonite solid form, which form is then converted to calcite by known methods in the art, for example by exposing the form to high temperature under vacuum.

Any method for conversion of aragonite to calcite as known in the art may be used to prepare calcite solid substrates of this invention.

In some embodiments, coral-based solid substrates of this invention may be converted to partially or fully into hydroxyapatite by known methods.

In some embodiments, coral-based solid substrates of this invention may be converted to partially or fully into hydroxyapatite by known methods.

In some embodiments, the solid substrates of this invention comprise a series of voids, and the at least two phases present in the scaffolding of this invention vary in terms of the average diameter of the voids present in each phase. In some embodiments, the solid substrate will comprise at least a first phase, comprising voids having an average diameter ranging from about 60-160 µm. In some embodiments, the first phase comprises voids having an average diameter ranging from about 60-90 µm, or in some embodiments, from about 80-130 µm, or in some embodiments, from about 120-160 m.

In some embodiments, the solid substrate will comprise at least a second phase, comprising voids having an average diameter ranging from about 170-850 µm. In some embodiments, the second phase comprises voids having an average diameter ranging from about 170-400 µm, or in some embodiments, from about 250-500 µm, or in some embodiments, from about 450-700 µm or in some embodiments, from about 550-850 µm.

In some embodiments, according to this aspect, the solid substrate further comprises a third phase, comprising voids having an average diameter ranging from about 150-300 µm and said second phase comprises voids having an average diameter ranging from about 350-850 µm and said third phase is positioned between said first and second phase. In some embodiments, such at least third phases may be referred to herein interchangeably as an "intermediate phase".

In some embodiments, the solid substrate is cylindrical in shape and has a diameter of about 5-15 mm, and a height of about 5-25 mm. In some embodiments, the solid substrate has a diameter of about 1-35 mm, and a height of about 1-45 mm, or about 5-40 mm, and a height of about 5-60 mm, or about 5-15 mm, and a height of about 5-45 mm.

The average diameter of the voids within the phases of the scaffolding of this invention may be determined by any means, including digital images analysis, as exemplified further hereinbelow. In one embodiment, a coral for use in a solid substrate of this invention comprises an average void diameter appropriate for cell seeding and/or development of vasculature.

The solid forms of this invention comprise at least three phases, two of which phases contain pores, owing to the porous nature of the materials of which the scaffolding is comprised. In some embodiments, the phases vary in terms of the pore volume (porosity) in each phase.

It will be appreciated that different species of coral vary in terms of their average pore diameter and pore volume and the invention contemplates use of any such coral as a starting material for the preparation of the solid substrates as herein described.

By optimizing the specific positioning of a solid substrate the porous crystalline structure of a coral solid substrates of this invention, described below, is accessible to beneficial components located within a tissue milieu. For example, the porous crystalline structure of coral allows in-growth of blood vessels to create a blood supply for the cartilage that will infiltrate the solid substrate during cartilage repair. By penetrating into a bone marrow void, mesenchymal stem cells located within the bone marrow now have access to the exposed surface of the solid substrate. In one embodiment, the region of the solid substrate penetrating into a bone marrow void attracts mesenchymal stem cells from the bone marrow and promotes blood vessel formation to the site of cartilage repair. In one embodiment, the region of the solid substrate penetrating into a bone marrow void promotes adhesion, proliferation, or differentiation or a combination thereof, of the mesenchymal stem cells attracted to the solid substrate.

Thus, it will be apparent to one skilled in the art that the specific positioning of the solid substrate within a site of cartilage repair arranges the solid substrate of this invention such that the solid substrate is most effective for cartilage and bone repair.

In some embodiments, the improved solid substrates of this invention allow for greater solid substrate incorporation within newly developed cartilage, reduced inflammation at the implant site or a combination thereof.

In some embodiments, the solid substrate approximates the form of a cylinder, cone, tac, pin, screw, rectangular bar, plate, disc, pyramid, granule, ball or cube.

In some embodiments, the solid substrates of this invention may be used in conjunction with other known and/or available materials for stimulating/enhancing bone and/or cartilage repair. In some embodiments, the solid substrates of this invention may be utilized to affix additional solid substrates, for example for use in whole joint repair or ligament repair, or other connector tissue repair.

In some embodiments, the solid substrates of this invention may be used for example, as a pin, in conjunction with other solid substrates for bone repair or regeneration, etc. It is to be understood that any use of the solid substrates of this invention, alone or in conjunction with other appropriate materials, for the treatment, repair or stimulation of growth of bone and/or cartilage is to be considered as part of this invention It will be appreciated that the solid substrates of this invention may be of any suitable shape or size to accommodate its application in accordance with the methods of this invention. For example, and in some embodiments, for applications of the solid substrates of this invention within long bones of a subject, the dimensions of the solid substrate will be scaled to approximate that of the site into which the solid substrate will be implanted, and may be on an order of magnitude scaling from millimeters to centimeters, as needed. Similarly, shapes of the solid substrates of the invention may be any shape into which the solid substrates of this invention may be machined or processed, and may have any configuration as will be appropriate to achieve the desired growth, repair or regeneration of bone and/or cartilage.

In some embodiments, the invention provides a kit for the repair, regeneration or enhancement of formation of cartilage, bone, or a combination thereof comprising the solid substrates of this invention, directions for utilizing said solid substrate in the repair, regeneration or enhancement of formation of cartilage, bone, or a combination thereof and optionally a tool or tools for optimal insertion of said solid substrate, seeding said solid substrate with cells or a combination thereof.

In some embodiments, the kits of this invention comprise:
 a solid substrate comprising:
  a first phase comprising a marine organism skeletal derivative-based solid substrate comprising a series of hollows along a longitudinal axis in said first phase; and
  a second phase comprising a marine organism skeletal derivative-based solid substrate; and
 at least one biocompatible polymer.

According to this aspect, and in some embodiments, such kits are provided with instructions and appropriate tools for applying such biocompatible polymers to the solid substrate, such that, in some embodiments, some of the biocompatible polymer is substantially located within the series of hollows in the substrate. In other embodiments, such kits are provided with instructions and appropriate tools for applying such biocompatible polymers to the solid substrate, such that, in some embodiments, some of the biocompatible polymer creates a separate phase at a terminus of such solid substrate.

In one embodiment, the coral is seeded with a precursor cell. In one embodiment, the precursor cell is a mesenchymal stem cell. In other embodiments, the cell may be a mesenchymal cell; chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. In one embodiment of the present invention, the precursor cells for use in the method of the present invention are prepared from an organ tissue of the recipient mammal (i.e. autologous), or a syngeneic mammal. In another embodiment, allogeneic and xenogeneic precursor cells may be utilized.

In one embodiment, a site of cartilage repair may be considered to comprise a 3 dimensional (3-D) space at or proximal to a site of a cartilage and/or defect or potential defect. In one embodiment, this 3-D space comprises at least a wall or a floor, or a combination thereof, and positioning within such a site may be described herein, relative to said wall or floor, or in some embodiments, positioning may be relative to insertion within a tissue site proximal to said wall or floor. In some embodiments, positioning include insertion of the solid substrate or a region thereof, past the wall and/or floor of cartilage and/or bone tissue or a site of defect or injury or potential defect or injury in the cartilage and/or bone tissue, such that insertion into bone tissue occurs.

One skilled in the art will recognize that the shape of a site of cartilage and/or bone repair and the shape of a 3-D solid substrate of this invention provide many different combinations for stably positioning a solid substrate within a site of cartilage repair and/or bone. In one embodiment, a solid substrate of this invention is shaped prior to use in methods of this invention for cartilage repair and/or bone. In one embodiment, a solid substrate of this invention is shaped concurrent to use in methods of this invention for cartilage and/or bone repair. By shaping a solid substrate concurrent with use of the solid substrate in methods of this invention, the dimensions of the solid substrate may be precisely selected for specific positioning of the solid substrate within a site of repair. It will be appreciated that multiple solid substrates of this invention may be placed within or shaped and placed within a site of cartilage and/or bone repair.

In some embodiments, reference to a "solid substrate", "implant" or "plug", as used herein refers to any embodiment or combined embodiments as herein described with regard to the solid substrates to be considered as being included in the described aspect of this invention. For example, reference to a "solid substrate" as used herein, is to be understood to refer to any embodiment of a solid substrate as described herein being applicable for the indicated purpose or containing the indicated attribute, etc.

In one embodiment, "solid substrate" refers to a shaped platform used for cartilage and/or bone repair, wherein the shaped platform provides a site for cartilage and/or bone regeneration. In one embodiment, the solid substrate is a temporary platform. In one embodiment, "temporary platform" refers to a natural degradation of a coral of this invention that occurs over time during cartilage and/or bone repair, wherein the natural fully or partially degradation of the coral may results in a change of solid substrate shape over time and/or change in solid substrate size over time.

In one embodiment, the coral is shaped in the form of the tissue to be grown. For example, the coral can be shaped as a piece of cartilaginous tissue, such as a meniscus for a knee or elbow; a joint; an articular surface of a bone, the rib cage, a hip, a pelvis, an ear, a nose, a ligament, the bronchial tubes and the intervertebral discs.

This invention provides, in some embodiments, coral solid substrates for use in repairing cartilage and/or bone tissue defects associated with physical trauma, or cartilage and/or bone tissue defects associated with a disease or disorder in a subject.

In one embodiment of this invention, the term "coral" refers to coral which is cut from a single piece of coral. In one embodiment, the coral has pore-like cavities or interstices.

In one embodiment, the coral solid substrate is shaped prior to use in a method of cartilage and/or bone repair. In one embodiment, the coral solid substrate is shaped concurrent with a method of cartilage and/or bone repair, e.g., the coral solid substrate may be shaped during surgery when the site of repair may be best observed, thus optimizing the shape of the solid substrate used.

In one embodiment, the solid substrates, methods and/or kits of this invention employ use of a coral. In one embodiment, the coral comprise any species, including, inter alia, *Porites, Acropora, Goniopora, Millepora*, or a combination thereof.

In one embodiment, the coral is from the *Porites* species. In one embodiment, the coral is *Porites Lutea*. In most species, the void to solid ratios is generally in the range of 0.4 to 0.6, and the void phase completely interconnects, forming a highly regular network that interpenetrates the solid calcium carbonate phase. In one embodiment, this uniform and interconnecting architecture is particularly useful as a framework in the solid substrates, methods and/or kits of this invention.

In one embodiment, the coral is from the *Goniopora* species. In some embodiments, the coral is *Goniopora albiconus, Goniopora burgosi, Goniopora cellulosa, Goniopora ceylon, Goniopora ciliatus, Goniopora columna, Goniopora djiboutiensis, Goniopora eclipsensis, Goniopora fruticosa, Goniopora gracilis, Goniopora klunzingeri, Goniopora lobata, Goniopora mauritiensis, Goniopora minor, Goniopora norfolkensis, Goniopora palmensis, Goniopora pandoraensis, Goniopora parvistella, Goniopora pearsoni, Goniopora pendulus, Goniopora planulata, Goniopora polyformis, Goniopora reptans, Goniopora savignyi, Goniopora somaliensis, Goniopora stokes, Goniopora stutchburyi, Goniopora sultani, Goniopora tenella, Goniopora tenuidens* or *Goniopora viridis*.

In another embodiment, the coral is from any one or more of the following species *Favites halicora; Goniastrea retiformis; Acanthastrea echinata; Acanthastrea hemprichi; Acanthastrea ishigakiensis; Acropora aspera; Acropora austera; Acropora* sp. "brown digitate"; *Acropora carduus; Acropora cerealis; Acropora chesteifieldensis; Acropora clathrata; Acropora cophodactyla; Acropora* sp. "danai-like"; *Acropora divaricata; Acropora donei; Acropora echinata; Acropora efflorescens; Acropora gemmifera; Acropora globiceps; Acropora granulosa; Acropora* cf *hemprichi; Acropora kosurini; Acropora* cf *loisettae; Acropora longicyathus; Acropora loripes; Acropora* cf *lutkeni; Acropora paniculata; Acropora proximalis; Acropora rudis; Acropora selago; Acropora solitaryensis; Acropora* cf *spicifera* as per *Veron; Acropora* cf *spicifera* as per Wallace; *Acropora tenuis; Acropora valenciennesi; Acropora vaughani; Acropora vermiculata; Astreopora gracilis; Astreopora myriophthalma; Astreopora randalli; Astreopora suggesta; Australomussa rowleyensis; Coscinaraea collumna; Coscinaraea crassa; Cynarina lacrymalis; Distichopora violacea; Echinophyllia echinata; Echinophyllia* cf *echinoporoides; Echinopora gemmacea; Echinopora hirsutissima; Euphyllia ancora; Euphyllia divisa; Euphyllia yaeyamensis; Favia rotundata; Favia truncatus; Favites acuticollis; Favities pentagona; Fungia granulosa; Fungia klunzingeri; Fungia mollucensis; Galaxea acrhelia; Goniastrea edwardsi; Goniastea minuta; Hydnophora pilosa; Leptoseris explanata; Leptoseris incrustans; Leptoseris mycetoseroides; Leptoseris scabra; Leptoseris yabei; Lithophyllon undulatum; Lobophyllia hemprichii; Merulina scabricula; Millepora dichotoma; Millepora exaesa; Millipora intricata; Millepora murrayensis; Millipora platyphylla; Monastrea curta; Monastrea colemani; Montipora caliculata; Montipora capitata; Montipora foveolata; Montipora meandrina; Montipora tuberculosa; Montipora* cf *vietnamensis; Oulophyllia laevis; Oxypora crassispinosa; Oxypora lacera; Pavona bipartita; Pavona venosa; Pectinia alcicomis; Pectinia paeonea; Platygyra acuta; Platygyra pini; Platygyra* sp "green"; *Platygyra verweyi; Podabacia* cf *lanakensis; Porites annae; Porites cylindrica; Pontes evermanni; Porites monticulosa; Psammocora digitata; Psammocora explanulata; Psammocora haimeana; Psammocora superficialis; Sandalolitha dentata; Seriatopora caliendrum; Stylocoeniella armata; Stylocoeniella guentheri; Stylaster* sp.; *Tubipora musica; Turbinaria stellulata*; or any coral known in the art, or a combination thereof.

In another embodiment, derivatives of marine animals such as coral, sponges, moluscs shells and other related organisms may be used in the solid substrates, methods and/or kits of this invention. Such derivatives may comprise, inter alia, derivatives of *Madreporaria, Helioporida* of the order *Coenothecalia, Tubipora* of the order *Stolonifera*,

*Millepora* of the order *Milleporina*, or others known in the art. In some embodiments, coral for use in the substrates, methods and/or kits of this invention may comprise scleractinian coral, including in some embodiments, *Goniopora* and others. In some embodiments, coral for use in the substrates, methods and/or kits of this invention may comprise *Alveoppora*. In some embodiments, coral for use in the substrates, methods and/or kits of this invention may comprise bamboo corals, including in some embodiments, coral from the family Isididae, genera Keratoisis, Isidella, and others.

In one embodiment of this invention, the term "coral" refers to coral which is cut from a single piece of coral.

In some embodiments, the solid substrate is of any desired shape.

In one embodiment, coral may be machined into a variety of configurations, and quite complex shapes such as cylindrical structures and threaded structures may be formed by appropriate machine or other processing, such as chemical processing. In another embodiment, coral may be shaped to form solid blocks, rods or granular forms. In one embodiment, coralline materials are shaped in such a way as to conform to the shape of a desired tissue structure or to fill gap and contour defects in a potential implantation site. In one embodiment, coral is implanted in an orientation that allows it to contact the maximum surface area of an adjacent-located tissue structure.

As described above, a solid substrate's region's ability to position and confine the solid substrate of this invention is dependent on the region's geometry and the geometry at the site of cartilage and/or bone repair where the solid substrate will be implanted. In one embodiment, the region's geometry comprises a sharp edge. In one embodiment, the region's geometry comprises a rounded edge. In one embodiment, the region's geometry comprises a jagged edge.

In one embodiment of this invention, an optimal depth and angle within a site of cartilage and/or bone repair comprise the depth and angle most beneficial for cartilage and/or bone repair. In one embodiment, the optimal depth and angle most beneficial comprise a position so that a solid substrate of this invention is accessible to a pool of mesenchymal stem cells, a tissue milieu, blood vessels, nutrients, an effector compound, or a therapeutic compound, or a combination thereof.

In one embodiment of this invention, the term "depth" refers to a measurement of a solid substrate of this invention extending from an imaginary line resting on the open surface of a repair site to a place beneath the tissue floor at a site of cartilage and/or bone repair.

It will be recognized by one skilled in the art that the depth of other regions of the solid substrate may not be below any tissue surface. For example, and in an embodiment of this invention, based on a site of cartilage repair shaped like a cylindrical pit, an imaginary line drawn to rest across the opening of the pit represents the top of the pit. In one embodiment, positioning of the solid substrate results in the entirety of the solid substrate being below the top of the pit and therefore at a depth below the imaginary line across the opening. In one embodiment, positioning of the solid substrate results in a portion of the solid substrate being flush with the top of the pit.

In some embodiments, multiple solid substrates are inserted to maximally occupy a defect site, such that each solid substrate material may be inserted at a different angle and/or shape and/or depth and/or porosity to accommodate proper insertion into the desired region within a site of cartilage and/or bone repair. It is to be understood that the reference to angles of positioning above may be with regard to one or more solid substrates inserted in a particular cartilage and/or bone defect site.

Contact between exposed surfaces of a solid substrate and tissue at or proximal to a site of cartilage and/or bone repair provides a bioactive surface which, in the methods of use of this invention may induce or enhance cartilage and/or bone repair. For example, in one embodiment, the exposed surface of a solid substrate provides a bioactive surface attracting mesenchymal stem cells. In another embodiment, the exposed surface provides a place for mesenchymal stem cell attachment, growth, proliferation, or differentiation, or a combination thereof, all processes which induce or enhance cartilage repair. In addition, the exposed surface of a solid substrate may attract blood vessels. Moreover, tissue at or proximal to a site of cartilage and/or bone repair may be a rich source of nutrients, effector compounds, therapeutic compounds, or a combination thereof, which may be beneficial in cartilage and/or bone repair so that contact between an exposed surface of a solid substrate and such tissue induces or enhances cartilage and/or bone repair.

Thus, it will be apparent to one skilled in the art that the specific positioning of the solid substrate within a site of cartilage and/or bone repair arranges the solid substrate of this invention such that the solid substrate is most effective for cartilage and/or bone repair.

In one embodiment, "solid substrate" refers to a shaped platform used for cartilage and/or bone repair, wherein the shaped platform provides a site for cartilage and/or bone formation and/or regeneration. In one embodiment, the solid substrate is a temporary platform. In one embodiment, "temporary platform" refers to a natural fully or partially degradation of a coral of this invention that occurs over time during cartilage repair, wherein the natural degradation of the coral may results in a change of solid substrate shape over time and/or a change in solid substrate size over time.

In one embodiment, the coral is shaped in the form of the tissue to be grown. For example, the coral can be shaped as a piece of cartilaginous or bony tissue, such as a meniscus for a knee or elbow; a joint; an articular surface of a bone, the rib cage, a hip, a pelvis, an ear, a nose, the bronchial tubes, the intervertebral discs, a ligament, a vertebra, the tibia, the femur, the shoulder and the jaw.

This invention provides, in some embodiments, coral solid substrates for use in repairing cartilage and/or bone tissue defects associated with physical trauma, or cartilage and/or bone tissue defects associated with a disease or disorder in a subject.

In one embodiment of this invention, the term "coral" refers to coral which is cut from a single piece of coral. In one embodiment, the coral has pore-like cavities or interstices.

In one embodiment, the coral solid substrate is shaped prior to use in a method of cartilage and/or bone repair. In one embodiment, the coral solid substrate is shaped concurrent with a method of cartilage and/or bone repair, e.g., the coral solid substrate may be shaped during surgery when the site of repair may be best observed, thus optimizing the shape of the solid substrate used.

In one embodiment, the size of a solid substrate may be any size that would be useful for the purposes of the present invention, as would be known to one skilled in the art. In one embodiment, the solid substrate or a portion thereof may be about the size of a site of cartilage and/or bone repair. In one embodiment, the solid substrate or a portion thereof may be about the size of a cartilage and/or bone defect so that the solid substrate may be placed within a site of cartilage and/or bone repair. In another embodiment, the solid substrate may be larger than the size of a cartilage and/or bone defect. For example, in one embodiment, the solid substrate of this invention may be larger than the size of a cartilage and/or bone defect, whereby the solid substrate may extend to a site of mesenchymal cell availability. In one embodiment, the solid substrate may be smaller than the size of a cartilage and/or bone defect.

In some embodiments, the total solid substrate size will be on a millimeter scale, for example, having at least one long axis of about 2-200 mm, or in some embodiments, about 1-18 mm, or in some embodiments, about 0.5 mm-3 mm, or in some embodiments, about 6-12 mm, or in some embodiments, about 10-15 mm, or in some embodiments, about 12-40 mm, or in some embodiments, about 30-100 mm, or in some embodiments, about 50-150 mm, or in some embodiments, about 100-200 mm.

In some embodiments the total solid substrate size will be on the centimeter scale, for example having at least one long axis of about 0.5-30 cm In one embodiment, the solid substrate may be about the same size as a tissue void at a site of tissue repair. This tissue void may be due to a cartilage and/or bone defect, cartilage and/or bone degeneration or may have been created artificially during methods of cartilage and/or bone repair or any combination thereof. In one embodiment, the tissue void comprises an absence of cartilage and/or bone tissue. In one embodiment, the solid substrate or a portion thereof may be the size of a cartilage and/or bone defect such that the solid substrate may be placed within a site of cartilage and/or bone repair to enhance cartilage and/or bone formation at the site of cartilage and/or bone repair. In another embodiment, the solid substrate may be larger than the size of a cartilage and/or bone defect so that the solid substrate may reach to a site of mesenchymal stem cell availability.

In some embodiments, a tight fit is desirable with regard to fitting the implant within the site of tissue repair, except that it is desirable that the solid substrate be below the upper void limit or flush with the same. According to this aspect, and in some embodiments, it may be desirable to taper a terminus of the solid substrates of this invention for easy insertion within a tight space for optimal tight fitting of the implant.

In one embodiment, the term "void" refers to a space not occupied. In the instant invention, for example, in one embodiment, a void may be a space in a solid substrate naturally not occupied. In one embodiment, a void may be a space not occupied at a site of repair. In one embodiment, a void may be a space not occupied within a solid substrate of the current invention. In one embodiment, a void may be a volume of a pore or a pore region.

In one embodiment, coral is washed, bleached, frozen, dried, sterilized or a combination thereof. In some embodiments, the coral is processed as exemplified further hereinunder. In some embodiments, the coral, once processed into the solid substrates of this invention are seeded with a desired population of cells or populations of cells, prior to implantation within a site of cartilage and/or bone repair.

In one embodiment, the multi-phasic solid substrate for the repair of cartilage is prepared by an appropriate process known such as for example, the process described in WO 2010/146575, fully incorporated by reference herein.

In one embodiment of this invention, the term "portion" refers to a limited part of a whole. In one embodiment, the term "portion" with regard to the surface exposed as a consequence of the methods of this invention refers to a limited part of a whole exposed surface. In one embodiment of this invention, the term "surface" refers to an exterior or upper boundary of an object.

In one embodiment of this invention, the term "exposed" refers to being open to the surrounding environment such that contact may occur between a solid substrate of this invention and the immersion media.

According to this aspect, and in other embodiments, the solid forms of this invention comprise multiple phases which phases differ in their pore volume, or which phases comprise voids which differ in terms of the average diameter of said voids, or a combination thereof.

In one embodiment, a solid substrate of this invention comprises a solid throughout a solid substrate. One skilled in the art will recognize that solid solid substrateing of this invention still comprises pore-like cavities and/or interstices.

In one embodiment, a solid substrate of this invention comprises a hollow along a Cartesian coordinate axis of a solid substrate. In one embodiment, the hollow is along a long axis of a solid substrate of this invention. In one embodiment, the term "hollow" refers to a cavity within a solid substrate of this invention. In one embodiment, the hollow comprises at least a single opening in the solid substrate such that the cavity is exposed to the external environment. In one embodiment, the hollow provides additional exposed surface area for a solid substrate of this invention.

In some embodiments, the solid substrates of this invention will comprise multiple hollows, which may be in any orientation, or in some embodiments, the solid substrates of this invention will comprise a network of hollows within solid substrates, or in some embodiments, multiple solid substrates are implanted into a repair site, wherein hollows of the solid substrates are aligned to form a network of hollows throughout the implanted solid substrates.

It will be appreciated by the skilled artisan that methods for selective creation of hollows or voids (which words may be used interchangeably throughout) within the solid substrates of this invention may be prepared by any means known to the skilled artisan, for example, in accordance with the methods as herein described, for example, by replacing immersion dipping of the portion of the solid substrate with drip application of the immersion solution to selectively create voids within the solid substrates of this application.

The exposed surface area of a solid substrate of this invention provides a location for mesenchymal stem cells, chondrocytes, osteoblasts, etc., attachment, growth, proliferation or differentiation, or a combination and a location for blood vessels formation. Therefore, the surface area of a solid substrate of this invention ultimately provides a beneficial location for regeneration of cartilage and/or bone tissue. In one embodiment of this invention, a solid substrate comprises a hollow, wherein the presence of the hollow increases the exposed surface area of a solid substrate compared to an analogous solid substrate without a hollow.

In one embodiment of this invention, the solid substrate comprises biocompatible polymers.

The term "biocompatible polymers" refers, in some embodiments, to the presence of a polymeric material in association with at least a portion of the scaffolding material, existing as part of the discrete phases as herein described.

In some embodiments, the solid substrate incorporates a biocompatible polymer therewithin, which is associated with the aragonite or calcite component, via any physical or chemical association. In some embodiments, the polymer is a part of a hydrogel, which is incorporated in the solid substrates of this invention. In some embodiments, such hydrogel-containing solid substrates may thereafter be lyophilized or dessicated, and may thereafter be reconstituted.

In one embodiment, the biocompatible polymers of this invention comprise a natural polymer comprising, collagen, elastin, silk, hyaluronic acid, sodium hyaluronate, cross linked hyalronic acid, chitosan, cross linked chitosan, alginate, calcium alginate, cross linked calcium alginate and any combinations thereof.

In one embodiment of this invention, a polymer comprises proteins such as zein, modified zein, casein, gelatin, gluten, serum albumin, collagen, actin, α-fetoprotein, globulin, macroglobulin, cohesin, laminin, fibronectin, fibrinogen, osteocalcin, osteopontin, osteoprotegerin, or others, as will be appreciated by one skilled in the art. In another embodiment, a polymer may comprise cyclic sugars, cyclodextrins, synthetic derivatives of cyclodextrins, glycolipids, glycosaminoglycans, oligosaccharide, polysaccharides such as alginate, carrageenan ($\chi$, $\lambda$, $\mu$, $\kappa$), chitosane, celluloses, condroitin sulfate, curdlan, dextrans, elsinan, furcellran, galactomannan, gellan, glycogen, arabic gum, hemicellulose, inulin, karaya gum, levan, pectin, pollulan, pullulane, prophyran, scleroglucan, starch, tragacanth gum, welan, xanthan, xylan, xyloglucan, hyaluronic acid, chitin, or a poly(3-hydroxyalkanoate)s, such as poly(β-hydroxybutyrate), poly(3-hydroxyoctanoate) or poly(3-hydroxyfatty acids), or any combination thereof.

In one embodiment, a polymer may comprise chemical derivatives thereof (substitutions, additions, and elimination of chemical groups, for example, alkyl, alkylene, hydroxylations, oxidations, and other modifications routinely made by those skilled in the art), blends of, e.g. proteins or carbohydrates alone or in combination with synthetic polymers.

In one embodiment of this invention, the polymer is biodegradable. In one embodiment, the term "biodegradable" or grammatical forms thereof, refers to a material of this invention, which is degraded in the biological environment of the subject in which it is found. In one embodiment, the biodegradable material undergoes degradation, during which, acidic products, or in another embodiment, basic products are released. In one embodiment, bio-degradation involves the degradation of a material into its component subunits, via, for example, digestion, by a biochemical process. In one embodiment, biodegradation may involve cleavage of bonds (whether covalent or otherwise), for example in a polymer backbone of this invention. In another embodiment, biodegradation may involve cleavage of a bond (whether covalent or otherwise) internal to a side-chain or one that connects a side chain to, for example a polymer backbone.

In one embodiment, a coral of this invention is covalently associated with the polymer via the use of a cross-linking agent. In one embodiment, the phrase "cross-linking agent" refers to an agent which facilitates the formation of a covalent bond between 2 atoms. In one embodiment, the cross-linking agent is a zero-length cross-linking agent.

In one embodiment, the cross-linking agent is (1 ethyl 3-(3dimethyl aminopropyl)carbodiimide (EDAC), N-Sulfohydroxy succinamide (Sulfo NHS), 5-iodopyrimidines, N-carbalkoxydihydroquinolines, pyrroloquinolinequinones, or a combination thereof.

In one embodiment, the cross-linking agent is a homobifunctional cross-linker, such as, for example, a N-hydroxysuccinimide ester (e.g. disuccinimidyl suberate or dithiobis (succinimidylpropionate), homobifunctional imidoester (e.g. dimethyladipimidate or dimethyl pimelimidate), sulfhydryl-reactive crosslinker (e.g. 1,4-di-[3'-(2'-pyridyldithio) propionamido]butane), difluorobenzene derivative (e.g. 1,5-difluoro-2,4-dinitrobenzene), aldehyde (e.g. formaldehyde, glutaraldehyde), bis-epoxide (e.g. 1,4-butanediol diglycidyl ether), hydrazide (e.g. adipic acid dihydrazide), bis-diazonium derivative (e.g. o-tolidine), bis-alkylhalide, or a combination thereof.

In one embodiment, the cross-linking agent is a heterobifunctional cross-linker, such as, for example, an aminereactive and sulfhydryl-reactive crosslinker (e.g. N-succinimidyl 3-(2-pyridyldithio)propionate, a carbonyl-reactive and sulfhydryl-reactive crosslinker (e.g. 4-(4-N-maleimidophenyl)butyric acid hydrazide), or a combination thereof.

In some embodiments, the cross-linking agent is a trifunctional cross-linkers, such as, for example, 4-azido-2-nitrophenylbiocytin-4-nitrophenyl ester, sulfosuccinimidyl-2-[6-biotinamido]-2-(p-azidobenzamido)hexanoamido] ethyl-1,3'-dithiopropionate (sulfo-SBED), or a combination thereof.

In another embodiment, the cross-linking agent is an enzyme. In one embodiment of this invention, the cross-linking agent comprises a transglutaminase, a peroxidase, a xanthine oxidase, a polymerase, or a ligase, or a combination thereof.

The choice of concentration of the cross-linking agent utilized for activity will vary, as a function of the volume, agent and polymer chosen, in a given application, as will be appreciated by one skilled in the art.

In one embodiment, the association of a coral of this invention with a biocompatible polymer of this invention comprises a physical and/or mechanical association. For example, in one embodiment, a physical and/or mechanical association may comprise imbibing of any means, air drying, using a cross-linking agent, applying of heat, applying vacuum, applying lyophilizing methods, freezing, applying mechanical forces or any combination thereof, to promote the physical association between a coral and a polymer coating as described herein.

In one embodiment, the thickness of the first phase containing the biocompatible polymer influences physical characteristics of a solid substrate of this invention. For example, the thickness of the polymer phase may influence elasticity, tensile strength, adhesiveness, or retentiveness, or any combination thereof of a solid substrate of this invention. In one embodiment, the thickness of the first phase containing the biocompatible polymer is selected so that it increases the elasticity of a solid substrate of this invention. In one embodiment, the thickness of the first phase containing the biocompatible polymer is selected so that it increases the tensile strength of a solid substrate of this invention. In one embodiment, the the thickness of the first phase containing the biocompatible polymer is selected so that it affects adhesion of mesencymal stem cells, blood vessels, tissue at a site of cartilage repair, cartilage tissue, or bone tissue, or a combination thereof. In one embodiment, the thickness of the first phase containing the biocompatible polymer is selected so that it decreases the adhesiveness of a solid substrate of this invention. In one embodiment, the thickness of the first phase containing the biocompatible polymer is selected so that it increases the adhesiveness of a solid substrate of this invention.

In one embodiment, the thickness of the first phase containing the biocompatible polymer is selected so that it influences proliferation and/or differentiation of mesenchymal stem cells applied to the solid substrates of this invention, or influences the activation or migration of cells associated with cartilage and/or bone formation or repair to the solid substrates of this invention, or a combination thereof.

In one embodiment of this invention, the cells as used in accordance with the solid substrates, methods of use or kits of this invention, are engineered to express a desired product.

In one embodiment, the biocompatible polymers of this invention comprise an effector compound. In one embodiment, the effector compound comprises a component of a kit of this invention for use for incorporation into a solid substrate of this invention as herein described. In one embodiment, the effector compound is applied directly to a polymer coating of this invention, without being dispersed in any solvent.

In one embodiment of this invention, the biocompatible polymers of this invention comprise an effector compound comprising a cytokine, a bone morphogenetic protein (BMP), growth factors, a chelator, a cell population, a therapeutic compound, or an antibiotic, or any combination thereof.

In one embodiment, effector compounds for use in a solid substrate and/or a kit of this invention and/or a method of this invention may comprise, inter-alia, a cytokine, a bone morphogenetic protein (BMP), growth factor, a chelator, a cell population, a therapeutic compound, an anti-inflammatory compound, a pro-angiogenic compound or an antibiotic, or any combination thereof.

In one embodiment, the phrase "a cell population" refers to a transfected cell population, a transduced cell population, a transformed cell population, or a cell population isolated from a subject, or a combination thereof. In some embodiments, transfected, transduced or transformed cells, may be incorporated into a polymer coat, or a solid substrate of this invention, or a combination thereof.

In one embodiment, transfected, transduced or transformed cells, may be incorporated into a polymer coating, or a solid substrate of this invention In one embodiment, a cell population of this invention comprises mesenchymal stem cells. In one embodiment, the mesenchymal stem cells are transformed. In one embodiment, a cell population comprises cells beneficial in cartilage and/or bone formation and/or repair, such as chondroblasts or chondrocytes; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In another embodiment, a precursor cell may refer to a combination of chondrocytes and other cells; a combination of osteocytes and other cells; a combination of synoviocytes and other cells; a combination of bone marrow cells and other cells; a combination of mesenchymal cells and other cells; a combination of stromal cells and other cells; a combination of stem cells and other cells; a combination of embryonic stem cells and other cells; a combination of precursor cells isolated from adult tissue and other cells; a combination of peripheral blood progenitor cells and other cells; a combination of stem cells isolated from adult tissue and other cells; and a combination of genetically transformed cells and other cells. the precursor cells for use in the method of the present invention are prepared from an organ tissue of the recipient mammal (i.e. autologous), or a syngeneic mammal. In another embodiment, allogeneic and xenogeneic precursor cells may be utilized.

In one embodiment of this invention, the phrase "a therapeutic compound" refers to a peptide, a protein or a nucleic acid, or a combination thereof. In another embodiment, the therapeutic compound is an antibacterial, antiviral, antifungal or antiparasitic compound. In another embodiment, the therapeutic compound has cytotoxic or anti-cancer activity. In another embodiment, the therapeutic compound is an enzyme, a receptor, a channel protein, a hormone, a cytokine or a growth factor. In another embodiment, the therapeutic compound is immunostimulatory. In another embodiment, the therapeutic compound inhibits inflammatory or immune responses. In one embodiment, the therapeutic compound comprises a pro-angiogenic factor.

In one embodiment, the phrase "a therapeutic compound", refers to a molecule, which when provided to a subject in need, provides a beneficial effect. In some cases, the molecule is therapeutic in that it functions to replace an absence or diminished presence of such a molecule in a subject. In one embodiment, the molecule is a nucleic acid coding for the expression of a protein is absent, such as in cases of an endogenous null mutant being compensated for by expression of the foreign protein. In other embodiments, the endogenous protein is mutated, and produces a non-functional protein, compensated for by the expression of a heterologous functional protein. In other embodiments, expression of a heterologous protein is additive to low endogenous levels, resulting in cumulative enhanced expression of a given protein. In other embodiments, the molecule stimulates a signaling cascade that provides for expression, or secretion, or others of a critical element for cellular or host functioning.

In another embodiment, the therapeutic compound may be natural or non-natural insulins, amylases, proteases, lipases, kinases, phosphatases, glycosyl transferases, trypsinogen, chymotrypsino gen, carboxypeptidases, hormones, ribonucleases, deoxyribonucleases, triacylglycerol lipase, phospholipase A2, elastases, amylases, blood clotting factors, UDP glucuronyl transferases, ornithine transcarbamoylases, cytochrome p450 enzymes, adenosine deaminases, serum thymic factors, thymic humoral factors, thymopoietins, growth hormones, somatomedins, costimulatory factors, antibodies, colony stimulating factors, erythropoietin, epidermal growth factors, hepatic erythropoietic factors (hepatopoietin), liver-cell growth factors, interleukins, interferons, negative growth factors, fibroblast growth factors, transforming growth factors of the α family, transforming growth factors of the β family, gastrins, secretins, cholecystokinins, somatostatins, serotonins, substance P, transcription factors or combinations thereof.

In one embodiment, the effector compound comprises, an anti-helminth, an antihistamine, an immunomodulatory, an anticoagulant, a surfactant, an antibody, a beta-adrenergic receptor inhibitor, a calcium channel blocker, an ace inhibitor, a growth factor, a hormone, a DNA, an siRNA, or a vector or any combination thereof.

In one embodiment, the phrase "effector compound" refers to any agent or compound, which has a specific purpose or application which is useful in the treatment, prevention, inhibition, suppression, delay or reduction of incidence of infection, a disease, a disorder, or a condition, when applied to the solid substrates, kits and/or methods of this invention. An effector compound of this invention, in one embodiment, will produce a desired effect which is exclusive to the ability to image the compound. In some embodiments, the effector compound may be useful in imaging a site at which the compound is present, however, such ability is secondary to the purpose or choice of use of the compound.

In one embodiment of this invention, term "effector compound" is to be understood to include the terms "drug" and "agent", as well, when referred to herein, and represents a molecule whose incorporation within the solid substrate and/or kits of this invention, or whose use thereof, is desired. In one embodiment, the agent is incorporated directly within a solid substrate, and/or kit of this invention. In another embodiment, the agent is incorporated within a solid substrate and/or kit of this invention, either by physical interaction with a polymer coating, a coral, or coral particles of this invention, and/or a kit of this invention, or association thereto.

In one embodiment, compounds for use in a solid substrate and/or a kit of this invention and/or a method of this invention may comprise, inter-alia, an antibody or antibody fragment, a peptide, an oligonucleotide, a ligand for a biological target, an immunoconjugate, a chemomimetic functional group, a glycolipid, a labelling agent, an enzyme, a metal ion chelate, an enzyme cofactor, a cytotoxic compound, a bactericidal compound, a bacteriostatic compound, a fungicidal compound, a fungistatic compound, a chemotherapeutic, a growth factor, a hormone, a cytokine, a toxin, a prodrug, an antimetabolite, a microtubule inhibitor, a radioactive material, or a targeting moiety, or any combination thereof.

In one embodiment, the solid substrates and/or kits of this invention and/or methods of this invention comprise or make use of an oligonucleotide, a nucleic acid, or a vector. In some embodiments, the term "oligonucleotide" is interchangeable with the term "nucleic acid", and may refer to a molecule, which may include, but is not limited to, prokaryotic sequences, eukaryotic mRNA, cDNA from eukaryotic mRNA, genomic DNA sequences from eukaryotic (e.g., mammalian) DNA, and even synthetic DNA sequences. The term also refers to sequences that include any of the known base analogs of DNA and RNA.

The solid substrates and/or kits of this invention and/or methods of use of this invention may comprise nucleic acids, in one embodiment, or in another embodiment, the solid substrates and/or kits of this invention and/or methods of use of this invention may include delivery of the same, as a part of a particular vector. In one embodiment, polynucleotide segments encoding sequences of interest can be ligated into commercially available expression vector systems suitable for transducing/transforming mammalian cells and for directing the expression of recombinant products within the transduced cells. It will be appreciated that such commercially available vector systems can easily be modified via commonly used recombinant techniques in order to replace, duplicate or mutate existing promoter or enhancer sequences and/or introduce any additional polynucleotide sequences such as for example, sequences encoding additional selection markers or sequences encoding reporter polypeptides.

In one embodiment, the solid substrate of this invention incorporates stem or progenitor or precursor cells. Such cells can be obtained directly from a mammalian donor, e.g., a patient's own cells, from a culture of cells from a donor, or from established cell culture lines. In some embodiments, the mammal is a mouse, rat, rabbit, guinea pig, hamster, cow, pig, horse, goat, sheep, dog, cat, monkey, ape or a human. Cells of the same species and/or of the same immunological profile can be obtained by biopsy, either from the patient or a close relative. Using standard cell culture techniques and conditions, the cells are then grown in culture until confluent and used when needed. The cells may be cultured until a sufficient number of cells have been obtained for a particular application.

In one embodiment, the solid substrate of this invention incorporates any cell which may participate in cartilage and/or bone formation or repair. In some embodiments, such cells represent autografts, in that cells are cultured ex-vivo to seed the cells on the solid substrates of the invention, and such seeded solid substrates are implanted into the subject.

In some embodiments, such cells may represent allografts or xenografts, which may be incorporated within the solid substrates of this invention and implanted within a site of repair.

In one embodiment, a coral of this invention comprises a cell population from in vitro culture of the coral for a time period sufficient to seed the cells in the coral. In one embodiment, the cell population is a mesenchymal stem cell population, chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof. In one embodiment, the mesenchymal stem cells; chondrocyte; fibrochondrocyte; osteocyte; osteoblast; osteoclast; synoviocyte; bone marrow cell; stromal cell; stem cell; embryonic stem cell; precursor cell, derived from adipose tissue; peripheral blood progenitor cell; stem cell isolated from adult tissue; genetically transformed cell; or a combination thereof seeded in vitro are transformed. In one embodiment, the cell population comprises a cell population beneficial for cartilage repair. In one embodiment, the culture comprises a chelator. In one embodiment of this invention, the chelator in a culture comprises a calcium chelator.

In some embodiments, the marine organism skeletal derivative is characterized by a specific fluid uptake capacity value of at least 75%, which specific fluid uptake capacity value is determined by establishing a spontaneous fluid uptake value divided by a total fluid uptake value.

According to this aspect, a specific fluid uptake capacity value may be determined by evaluating spontaneous uptake of a biologic fluid versus a total uptake capacity for a given sample and arriving at the specific fluid uptake capacity level, whereby if the value is over 75%, then such solid substrate will be used as described.

In some embodiments, the process for selection of the material for incorporation within a solid substrate of this invention comprises isolating a sample of a coralline-based solid material and establishing a specific fluid uptake capacity value of the material, which specific fluid uptake capacity value is determined as described.

In some embodiments, the biologic fluid is blood, and in some embodiments, the biologic fluid is water. In some embodiments, the biologic fluid is hydrophilic.

In some embodiments, the biologic fluid is autologous with respect to a cell or tissue of a subject when said solid substrate is contacted with such cell or tissue of said subject.

It will be understood that the biologic fluid may be any fluid which is biocompatible and whose incorporation is appropriate within a solid substrate for the desired application.

In some embodiments, the process further comprises the step of contacting the material with a fluid for from 2-15 minutes to promote spontaneous fluid uptake of said fluid within said coralline-based solid material to arrive at said spontaneous fluid uptake value. In some embodiments, the process may allow for the contacting of the material with a fluid for from 0.5-15 minutes, or in some embodiments, from 0.5-5 minutes, or in some embodiments, 10-60 minutes, or in some embodiments, from 60 to 90 minutes, or in some embodiments, other intervals, to promote spontaneous fluid uptake. The skilled artisan will appreciate that the amount of time for which the fluid is applied to determine the spontaneous uptake may be extended or shortened as a function of the dimensions and geometry of the sample substrate being assessed. In some embodiments, when a larger sample is being assessed, the process further comprises the step of contacting the material with a fluid for from 2-24 hours to promote spontaneous fluid uptake of said fluid within said coralline-based solid material to arrive at said spontaneous fluid uptake value In some embodiments, the process further comprises the step of contacting said marine organism skeletal derivative-based solid material with a fluid and applying negative pressure to said coralline-based solid material to promote maximal uptake of said fluid within said coralline-based solid material to arrive at said total fluid uptake value. In some embodiments, application of positive pressure is via the application of a vacuum to the substrate immersed in the fluid, promoting entry of the fluid therewithin.

In some embodiments, the process may further comprise the step of contacting said coralline-based solid material with a fluid and applying positive pressure to said coralline-based solid material to promote maximal uptake of said fluid within said coralline-based solid material to arrive at said total fluid uptake value. According to this aspect, and in some embodiments, care will be taken to ensure that the application of pressure does not in any way compromise the structural integrity of the solid substrate.

In some embodiments, application of positive pressure is via any manual means, for example, via the use of any applicator, syringe, etc., gravitational pressure, and others, as will be appreciated by the skilled artisan. In some embodiments, application of positive pressure is via forced osmosis, centrifugation and others. In some embodiments, combinations of the described methods and others are envisioned.

In some embodiments, the marine organism skeletal derivative is characterized by having a contact angle value of less than 60 degrees, when in contact with a fluid.

In some embodiments, the solid substrates characterized by a contact angle value of less than 60 degrees is comparable to samples having a specific fluid uptake capacity value of at least 75%.

Methods for determining a contact angle are well known, and any appropriate method can be used.

Such solid substrates may be converted to hydroxyapatite prior to or following such assessment of specific fluid uptake value or contact value, as described.

According to this aspect, and in one embodiment, some or all phases of the solid substrates as herein defined, such as, for example, coral samples or nacre or others as herein described are assessed by selecting a small dry sample for use in the processes as herein described, whose region of isolation from a larger block may be ascertained, in order to provide information regarding the characteristics of the area in the block from which additional samples may be isolated and then used.

In some aspects, the sample is dried under vacuum and/or heated or pressurized or steam treated.

In some embodiments, for aspects relating to a specific fluid uptake capacity value, such value is a function of change in weight in said coralline-based solid material.

According to this aspect and in some embodiments, the dry weight for each sample is recorded and fluid as described herein is added an assay container.

According to this aspect and in some embodiments, at least 1:1 ratio of the size of the sample in mm to the volume of fluid added in ml is applied to the container. In some embodiments, the amount of fluid applied is in excess, as compared to the sample size.

According to this aspect and in some embodiments, once the initial fluid uptake is assessed, according to this aspect and in some embodiments, the solid substrate sample is then brought into contact with the fluid and the weight of the solid substrate sample is assessed. In other embodiments the specific gravity is assessed by gradient centrifugation of by the Archimedean principle.

According to this aspect and in some embodiments, spontaneous fluid uptake is assessed and a spontaneous fluid uptake value is established, based on the change in weight of the sample.

According to this aspect and in some embodiments, the specific fluid uptake capacity value is a function of change in fluid volume of applied fluid to said marine organism skeletal derivative-based solid material. According to this aspect, spontaneous fluid uptake is assessed and a spontaneous fluid uptake value is established based on the complete uptake of the volume applied to the sample.

According to this aspect and in some embodiments, the process then further comprises contacting a significantly increased amount of fluid with the sample and applying pressure thereto to promote maximal fluid uptake to the total fluid uptake capacity of the sample.

According to this aspect and in some embodiments, as noted, such pressure may be either positive or negative pressure, and the application time is for a period of time sufficient to ensure maximal uptake of the applied fluid into the marine organism skeletal derivative sample.

According to this aspect and in some embodiments, such time may include an interval of from 0.5-60 minutes, or in some embodiments, when a larger sample is being assessed, such time may include an interval of from 2-24 hours to to arrive at said spontaneous fluid uptake value. It will be appreciated that the time intervals recited herein are applicable for any embodiment with regard thereto as described herein. The skilled artisan will appreciate that the amount of time for which the fluid is applied to determine the full capacity fluid uptake may be extended or shortened as a function of the dimensions and geometry of the sample substrate being assessed.

According to these aspects, the total fluid uptake capacity is thus assessed and the specific fluid uptake capacity value is then determined.

In some embodiments, the invention specifically contemplates solid substrates having a specific fluid uptake capacity value exceeding the cutoff value of 75%, for the sample to be noted optimized as a solid substrate for promoting cell or tissue growth. It will be appreciated that the invention contemplates the stated cutoff value for promoting a reasonable value that reduces the presence of appreciable false positives, i.e. solid substrates that are not as optimal for the stated applications.

In some embodiments, the invention specifically contemplates solid substrates characterized by one or more phases therein comprising a marine organism skeletal derivative having a contact angle value of less than 60 degrees, when in contact with a fluid. It will be appreciated that the invention contemplates the stated cutoff value for promoting a reasonable value that reduces the presence of appreciable false positives, i.e. solid substrates that are not as optimal for the stated applications.

In some embodiments, when the sample is utilized in vivo in subsequent applications, in some aspects, the sample is first contacted with autologous biological fluids or materials from the host prior to implantation into the same, verifying the observed enhanced fluid uptake phenotype as herein described.

In other embodiments the substrate may be a mixture of several marine originated materials or a mixture of bone and coral granules or cartilage and coral granules. In some embodiments, the solid substrate may be a composite material comprised of multiple samples of the marine organism skeletal derivatives as herein described.

In some embodiments, according to this aspect, the invention provides a method of inducing or enhancing repair, regeneration or enhancement of formation of cartilage, bone or a combination thereof, said method comprising implanting in a subject, a solid substrate as herein described within a site in need of repair, regeneration or enhancement of formation of cartilage, bone or a combination thereof.

In some embodiments, the invention provides a method of inducing or enhancing repair, regeneration or enhancement of formation of cartilage, bone or a combination thereof, said method comprising:
   implanting within a site in need of repair, regeneration or enhancement of formation of cartilage, bone or a combination thereof in a subject, a solid substrate comprising:
      a first phase comprising marine organism skeletal derivative-based solid substrate comprising a first biocompatible polymer and said first phase further comprises a series of hollows along a longitudinal axis in said first phase, wherein said first biocompatible polymer is substantially located within said series of hollows; and
      a second phase comprising marine organism skeletal derivative-based solid substrate, optionally comprising a series of hollows along a longitudinal axis in said second phase;
   whereby said implanting places said solid substrate below an upper limit of said site in need of repair, and
   applying a second biocompatible polymer to a region above said first phase to be slightly below, to be flush with or to slightly exceed an upper limit of said site in need of repair.

In one embodiment, the phrase "cartilage repair" refers to restoring a cartilage defect to a more healthful state. In one embodiment, restoring cartilage results in regeneration of cartilage tissue. In one embodiment, restoring cartilage results in regeneration of a full or partial thickness articular cartilage defect. In one embodiment, restoring cartilage results in complete or partial regeneration of cartilage tissue at a site of cartilage repair. In one embodiment, cartilage repair may result in restoration/repair of missing or defective bone tissue, wherein repair of a cartilage defect necessitates removal of bone tissue at a site of cartilage repair. In one embodiment, restoring cartilage results in regeneration of osteochondral defect. In one embodiment, cartilage repair comprises restoring cartilage defects of joints (e.g. knee, elbow, hip, shoulder joints), of ears, of a nose, or of a wind pipe.

In one embodiment, the phrase "bone repair" refers to restoring a bone defect to a more healthful state. In one embodiment, restoring bone results in regeneration of bone tissue. In one embodiment, restoring bone results in the filling in of any fracture or void within a bone tissue. In one embodiment, restoring bone results in complete or partial regeneration of bone tissue at a site of bone repair. In one embodiment, bone repair may result in restoration/repair of missing or defective bone tissue. In one embodiment, bone repair comprises restoring bone defects of any bone, as needed.

In some embodiments, the phrase "bone repair" refers to the treatment of a subject with osteoporosis, Paget's disease, fibrous dysplasias, or osteodystrophies. In another embodiment, the subject has bone and/or cartilage infirmity. In another embodiment, the subject has other bone remodeling disorders include osteomalacia, rickets, rheumatoid arthritis, achondroplasia, osteochodrytis, hyperparathyroidism, osteogenesis imperfecta, congenital hypophosphatasia, fribromatous lesions, multiple myeloma, abnormal bone turnover, osteolytic bone disease, periodontal disease, or a combination thereof. In one embodiment, bone remodeling disorders include metabolic bone diseases which are characterized by disturbances in the organic matrix, bone mineralization, bone remodeling, endocrine, nutritional and other factors which regulate skeletal and mineral homeostasis, or a combination thereof. Such disorders may be hereditary or acquired and in one embodiment, are systemic and affect the entire skeletal system.

The solid substrates, kits and methods of the invention may also be used to enhance bone and/or cartilage formation in conditions where a bone and/or cartilage deficit is caused by factors other than bone remodeling disorders. Such bone deficits include fractures, bone trauma, conditions associated with post-traumatic bone surgery, post-prosthetic joint surgery, post plastic bone surgery, bone chemotherapy, post dental surgery and bone radiotherapy. Fractures include all types of microscopic and macroscopic fractures. In one embodiment, some examples of fractures includes avulsion fracture, comminuted fracture, transverse fracture, oblique fracture, spiral fracture, segmental fracture, displaced fracture, impacted fracture, greenstick fracture, torus fracture, fatigue fracture, intraarticular fracture (epiphyseal fracture), closed fracture (simple fracture), open fracture (compound fracture) and occult fracture. In one embodiment, fractures meant to be treated using the methods of the present invention are non-union fractures.

In one embodiment, the solid substrates, kits and methods of the invention may also be used to augment long bone fracture repair; generate bone in segmental defects; provide a bone graft substitute for fractures; facilitate tumor reconstruction or spine fusion; provide a local treatment (by injection) for weak or osteoporotic bone, such as in osteoporosis of the hip, vertebrae, or wrist, or a combination thereof. In another embodiment, the solid substrates, kits and methods of the invention may also be used in a method to accelerate the repair of fractured long bones; treat of delayed union or non-unions of long bone fractures or pseudoarthrosis of spine fusions; induce new bone formation in avascular necrosis of the hip or knee, or a combination thereof.

In one embodiment, a method of this invention comprises inducing and enhancing cartilage and/or bone repair wherein implanting a solid substrate of this invention within a site of cartilage and/or bone repair influences and improves cartilage and/or bone repair.

In one embodiment, a method of this invention induces or enhances cartilage and/or bone repair, wherein the solid substrate attracts a population of cells to the solid substrate, thereby influencing or improving cartilage and/or bone repair.

The 3-D architecture and chemical composition of a solid substrate of this invention are of great importance for specifically positioning and confining a solid substrate within a site of cartilage and/or bone repair; for cellular recognition, adhesion, proliferation and differentiation of cell populations which induce or enhance cartilage and/or bone repair or a combination thereof.

In one embodiment, a solid substrate of this invention utilized in a method of this invention comprises a seeded cell population prior to being implanted in a subject. In one embodiment, a method of this invention induces or enhances cartilage and/or bone repair, wherein implanting in a subject a solid substrate of this invention promotes adhesion, proliferation or differentiation, or a combination thereof of transformed mesenchymal stem cells. In one embodiment, a method of this invention induces or enhances cartilage and/or bone repair, wherein implanting in a subject a solid substrate of this invention promotes blood vessel formation.

In one embodiment, a solid substrate utilized in a method of the present invention may be used to adsorb or bind, and deliver, other therapeutically active substances which assist in the cartilage and/or bone repair or regeneration process, or which have other desired therapeutic activity. Such substances include, by way of example, known synthetic or semisynthetic antibiotics which may be introduced into the pore cavities of the shaped product or structure, or a growth factor such as transforming growth factor or one of the bone morphogenic proteins which can be used to assist or promote bone growth.

In any of the embodiments herein, solid substrates for use in the methods of the present invention may further comprise, or be implanted with, other compounds such as, for example, antioxidants, growth factors, cytokines, antibiotics, anti-inflammatories, immunosuppressors, preservative, pain medication, other therapeutics, and excipient agents. In one embodiment, examples of growth factors that may be administered in addition to the HMG-CoA reductase inhibitor include, but are not limited to, epidermal growth factor (EGF), transforming growth factor-alpha (TGF-β), transforming growth factor-beta (TGF-β), human endothelial cell growth factor (ECGF), granulocyte macrophage colony stimulating factor (GM-CSF), bone morphogenetic protein (BMP), nerve growth factor (NGF), vascular endothelial growth factor (VEGF), fibroblast growth factor (FGF), insulin-like growth factor (IGF), cartilage derived morphogenetic protein (CDMP), platelet derived growth factor (PDGF), or any combinations thereof. Examples of antibiotics include antimicrobials and antibacterials.

In one embodiment, a method of this invention comprises implanting a solid substrate of this invention in a subject afflicted with a cartilage and/or bone defect or disorder or disease.

In one embodiment, the term "implanting" refers to inserting and fixing a solid substrate of this invention within a living site in a subject, the site comprising a site of cartilage and/or bone repair. In one embodiment, a method of this invention implants a solid substrate such a region of the solid substrate now has access to mesenchymal stem cells, nutrients, blood vessels, or effector compounds, or any combination there of. In one embodiment, a method of this invention comprises implanting in a subject a solid substrate of this invention, wherein the method results in removing a region of cartilage and/or bone and/or other tissue so that a region of the solid substrate penetrates through the cartilage and/or bone and/or other tissue, and in some embodiments, reaches a bone marrow void.

A clinician skilled in the art will recognize that methods of this invention, which entail implanting a solid substrate within a site of cartilage and/or bone repair, may require preparation of a site of cartilage and/or bone repair. These preparations may occur prior to implantation of a solid substrate or simultaneously with implantation. For example, cartilage and/or bone tissue and/or other tissues proximal to a site of cartilage and/or bone repair may initially be drilled through to create a channel of dimensions appropriate for a solid substrate used in the methods of this invention. Then the solid substrate is implanted within the site so that a region of the solid substrate penetrates the drilled cartilage and/or bone tissues. Alternatively, the solid substrate may be attached to a tool of this invention capable of penetrating through cartilage and/or bone or other tissues, or a combination thereof. In this case, as the tool penetrates through the cartilage and/or bone tissue, the attached solid substrate is simultaneously implanted.

In some embodiments, following implantation of the solid substrate within a repair site, or several solid substrates within the repair site, the solid substrate is processed to optimize incorporation and optimal cartilage and/or bone repair. In some embodiments, such processing may comprise cutting, sanding or otherwise smoothing the surface of the solid substrate or solid substrates, for optimal repair.

In one embodiment, methods of this invention comprise implanting a solid substrate in a human subject.

In one embodiment of this invention, the phrases "long axis of the solid substrate" and longitudinal axis of the solid substrate" are used interchangeably and refer to a line extending parallel to the solid substrate lengthwise. The term "lengthwise" refers the direction of the length of a solid substrate. It may be that an original geometric shape has been cut to produce a horizontal section of the original solid substrate. In such instances lengthwise should be viewed as being the original direction of length along a solid substrate.

It will be apparent to one skilled in the art that the physical and/or chemical properties of a solid substrate of this invention and components thereof may influence methods of use of this invention and kits thereof, for inducing or enhancing cartilage and/or bone repair.

In one embodiment, methods of this invention for inducing or enhancing cartilage and/or bone repair utilize the 3-D geometry of a solid substrate of this invention to provide for specifically positioning and confining the solid substrate within a site of cartilage and/or bone repair.

One skilled in the art will recognize that the shape of a site of cartilage and/or bone repair and the shape of a 3-D solid substrate of this invention provide many different combinations for stably positioning a solid substrate within a site of cartilage and/or bone repair. In one embodiment, a solid substrate of this invention is shaped prior to use in methods of this invention for cartilage and/or bone repair. In one embodiment, a solid substrate of this invention is shaped concurrent to use in methods of this invention for cartilage and/or bone repair. By shaping a solid substrate concurrent with use of the solid substrate in methods of this invention, the dimensions of the solid substrate may be precisely selected for specific positioning of the solid substrate within a site of repair.

In one embodiment, methods of this invention comprise implanting a solid substrate in a non-human mammalian and non-mammalian subject. In one embodiment, methods of this invention comprise implanting a solid substrate in a horse, a race horse, a cow, a steer, a pig, a rabbit, a goat, a sheep, a farm animal, a pet, a dog, a cat, a monkey, an ape, a bird and an aves In one embodiment, methods of this invention are utilized for induced or enhanced repair of a cartilage and/or bone defect or disorder or disease. In one embodiment, the cartilage defect results from a trauma, a tear, a sports injury, a full thickness articular cartilage defect, a joint defect, or a repetitive stresses injury (e.g., osteochondral fracture, secondary damage due to cruciate ligament injury). In one embodiment, the cartilage disorder comprises a disease of the cartilage. In one embodiment, methods of this invention induce or enhance cartilage repair in osteoarthritis, rheumatoid arthritis, aseptic necrosis, osteochondritis dissecans, articular cartilage injuries, chondromalacia patella, chondrosarcoma, chondrosarcoma-head and neck, costochondritis, enchondroma, hallux rigidus, hip labral tear, osteochondritis dissecans, torn meniscus, relapsing polychondritis, canine arthritis, fourth branchial arch defect or cauliflower ear. In one embodiment, methods of this invention induce or enhance cartilage repair in degenerative cartilagenous disorders comprising disorders characterized, at least in part, by degeneration or metabolic derangement of connective tissues of the body, including not only the joints or related structures, including muscles, bursae (synovial membrane), tendons, and fibrous tissue, but also the growth plate, meniscal system, and intervertebral discs.

In one embodiment, the 3-D shape and chemical composition of a solid substrate of this invention, used in the methods and/or kits of this invention will be determined by skilled clinicians, based on factors such as exact nature of the condition being treated, the severity of the condition, the age and general physical condition of the subject, body weight, and response of the individual subject, etc.

In one embodiment, the specific positioning of a solid substrate of this invention during methods of this invention will be determined by skilled clinicians, based on factors such as exact nature of the condition being treated, the severity of the condition, the age and general physical condition of the subject, body weight, and response of the individual subject, etc.

In one embodiment, methods of this invention are evaluated by examining the site of cartilage and/or bone tissue repair, wherein assessment is by histology, histochemistry, palpation, biopsy, endoscopy, arthroscopy, or imaging techniques comprising X-ray photographs, computerized X-ray densitometry, computerized fluorescence densitometry, CT, MRI or another method known in the art, or any combination thereof.

In one embodiment, this invention provides a kit for repair of tissue comprising the solid substrate of this invention, and directions for utilizing the solid substrate in tissue repair.

One skilled in the art will recognize that choice of a kit by a skilled clinician would be dependent upon factors such as exact nature of the condition being treated, the severity of the condition, the age and general physical condition of the subject, body weight, and response of the individual subject.

Thus, in one embodiment, the solid substrate comprised in a kit of this invention comprises different sizes, shapes or chemical compositions, or a combination thereof. In one embodiment, this invention provides a kit for cartilage and/or bone repair comprising a solid substrate of this invention, at least a tool of this invention, and directions for utilizing the solid substrate in cartilage repair.

It will be apparent to those skilled in the art that various modifications and variations can be made in the solid substrates, kits, process and methods of the present invention without departing from the spirit or scope of the invention.

In some embodiments, the term "comprise" or grammatical forms thereof, refers to the inclusion of the indicated components of this invention, as well as inclusion of other active agents, and pharmaceutically acceptable carriers, excipients, emollients, stabilizers, etc., as are known in the pharmaceutical industry.

In one embodiment, the present invention provides combined preparations. In one embodiment, the term "a combined preparation" defines especially a "kit of parts" in the sense that the combination partners as defined above can be used independently or in different combinations i.e., simultaneously, concurrently, separately or sequentially.

EXAMPLES

Example 1

Applications of Coralline-Based Scaffolding of this Invention

Coralline-based scaffolding of this invention may be inserted into cartilage, bone or a combination thereof, in a subject in need thereof.

In some embodiments, such placement will include drilling in the area to expose the site in which implantation is desired, and tight fitting of the solid substrate within the defect/site.

For implantation for cartilage repair, regeneration, etc., solid substrates are implanted in the desired cartilage site, and within proximally located bone, so that, in this way, the coral solid substrate is grafted through two types of tissue, cartilage and bone.

Figure 4B:
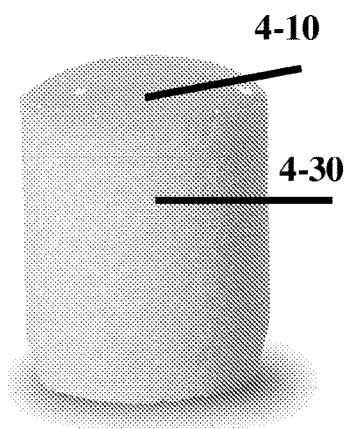
Figure 5:
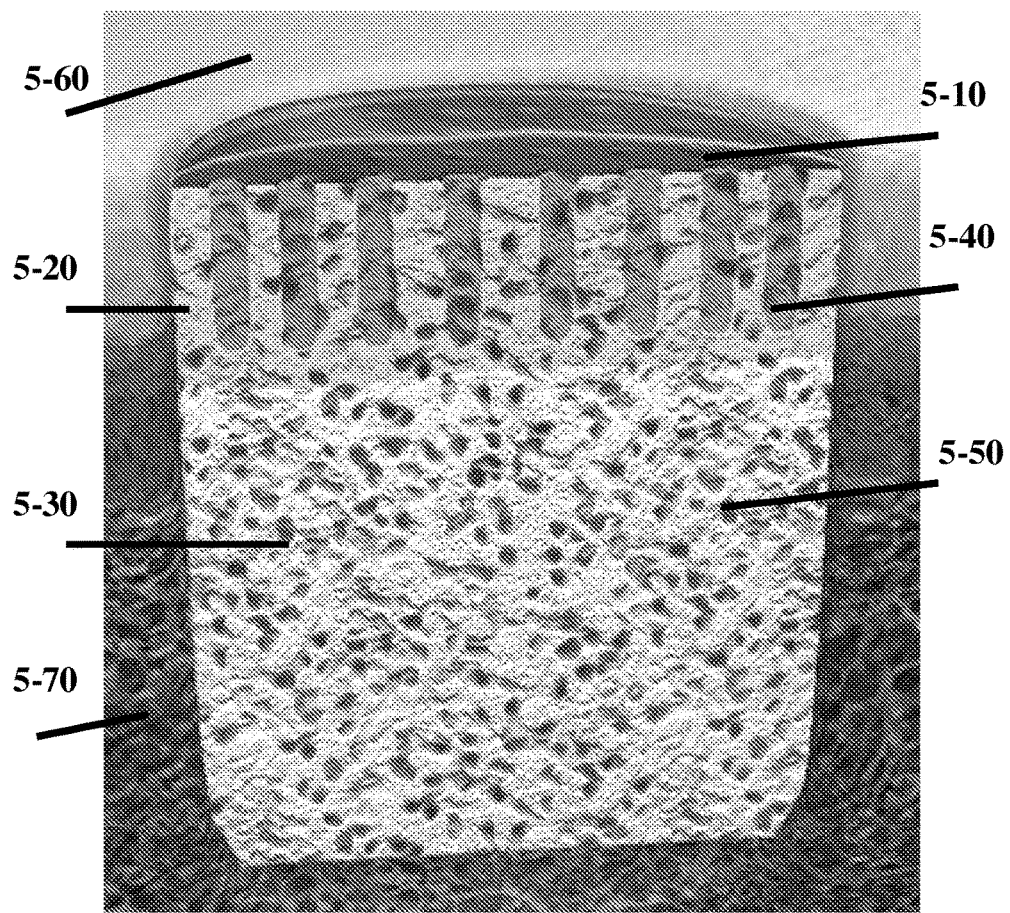
FIG. 5 schematically depicts the insertion of an embodied solid substrate within a defect site spanning bone 5-70 and cartilage 5-60. The first phase 5-10 and second phase 5-20 are both located within the cartilage layer, whereas the third phase 5-30 is located within the bone component. The voids within the second layer 5-40 are depicted, as well, but in this aspect, penetration of the biocompatible polymer therewithin is not readily seen. The diagram depicts the incorporation of appropriate cells within the implant 5-50 responsible for tissue regeneration and repair at the implantation site, as well.

FIGS. 1-3 schematically depicts illustrations of embodied solid substrates of this invention, indicating the presence of the first, second and third phases, respectively (1-10, 2-10 and 3-10; 1-20, 2-20 and 2-20; and 1-30, 2-30 and 3-30). The series of hollows 2-40 is evident, as is its impregnation with the second biocompatible polymer 2-45. FIG. 4 provides photographs of embodied scaffolds of this invention, with the threes phases indicated, in 4-10, 4-20 and 4-30. FIG. 5 schematically depicts the orientation of a cartoon of a solid substrate of this invention within a site of cartilage/bone repair.

Solid substrates may be prepared according to any embodiment as described herein, as will be appreciated by the skilled artisan.

The solid substrates are envisioned for use in veterinary applications, as well as in the treatment of human subjects. It is to be understood that animal studies may be undertaken to determine optimum configurations and implantation parameters and procedures.

For example, animal studies may include implantation of a solid substrate as described herein within an animal subject and solid substrates are examined and observed over an extended time period, post surgery. The untreated knee of each animal is used as a control for comparisons following such surgeries. At appropriate intervals, animals are sacrificed and histology performed. Appropriate time periods for examining the site of cartilage repair are 2.5, 4, 9, 12, 26, 52 weeks post surgery. At this time, the articular surfaces are photographed and tissue is removed from the site of repair and prepared for histological observations. Specifically, a block consisting of the grafted area and the surrounding tissue is removed using a fine saw. The material is further processed for routine histology, which includes slow decalcification.

It will be understood by those skilled in the art that various changes in form and details may be made therein without departing from the spirit and scope of the invention as set forth in the appended claims. Those skilled in the art will recognize, or be able to ascertain using no more than routine experimentation, many equivalents to the specific embodiments of the invention described herein. Such equivalents are intended to be encompassed in the scope of the claims.

In one embodiment of this invention, "about" refers to a quality wherein the means to satisfy a specific need is met, e.g., the size may be largely but not wholly that which is specified but it meets the specific need of cartilage repair at a site of cartilage repair. In one embodiment, "about" refers to being closely or approximate to, but not exactly. A small margin of error is present. This margin of error would not exceed plus or minus the same integer value. For instance, about 0.1 micrometers would mean no lower than 0 but no higher than 0.2. In some embodiments, the term "about" with regard to a reference value encompasses a deviation from the amount by no more than 5%, no more than 10% or no more than 20% either above or below the indicated value.

In the claims articles such as "a,", "an" and "the" mean one or more than one unless indicated to the contrary or otherwise evident from the context. Claims or descriptions that include "or" or "and/or" between members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention also includes embodiments in which more than one, or all of the group members are present in, employed in, or otherwise relevant to a given product or process. Furthermore, it is to be understood that the invention provides, in various embodiments, all variations, combinations, and permutations in which one or more limitations, elements, clauses, descriptive terms, etc., from one or more of the listed claims is introduced into another claim dependent on the same base claim unless otherwise indicated or unless it would be evident to one of ordinary skill in the art that a contradiction or inconsistency would arise. Where elements are presented as lists, e.g. in Markush group format or the like, it is to be understood that each subgroup of the elements is also disclosed, and any element(s) can be removed from the group. It should be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not in every case been specifically set forth in haec verba herein. Certain claims are presented in dependent form for the sake of convenience, but Applicant reserves the right to rewrite any dependent claim in independent format to include the elements or limitations of the independent claim and any other claim(s) on which such claim depends, and such rewritten claim is to be considered equivalent in all respects to the dependent claim in whatever form it is in (either amended or unamended) prior to being rewritten in independent format.

What is claimed is:

1. A solid substrate for tissue repair, said solid substrate consisting essentially of three phases wherein:

a first phase of said three phases consisting essentially of a first biocompatible polymer, which first phase is characterized by being comprised of an elastic material that is less rigid in structure than that of said substrate's second and third phases;

a second phase of said three phases consisting essentially of a marine organism skeletal derivative-based solid substrate and a second biocompatible polymer, wherein said second phase has a series of hollows along a longitudinal axis in said second phase, and wherein said second biocompatible polymer is substantially located within said series of hollows; and a third phase of said three phases consisting essentially of a marine organism skeletal derivative-based solid substrate, optionally having a series of hollows along a longitudinal axis in said third phase, wherein the first or second biocompatible polymer, or both the first and second biocompatible polymers, comprises hyaluronic acid, sodium hyaluronate, or a cross linked hyaluronic acid or a combination thereof, wherein said first or second biocompatible polymer or a combination thereof optionally contains a cytokine, a growth factor, a chelator, a cell population, a therapeutic compound, a drug, or any combination thereof, wherein said marine organism skeletal derivative-based solid substrate is a coral or coral derivative.

2. The solid substrate of claim 1, wherein said first phase is elastic following wetting in situ.

3. The solid substrate of claim 1, wherein said first or said second biocompatible polymer contains collagen, crosslinked collagen, chitosan, elastin, silk, alginate, polyethylene glycol, fibrin, platelet rich plasma, or combinations thereof.

4. The solid substrate of claim 3,
wherein said alginate contains calcium alginate, cross linked calcium alginate or a combination thereof, or
wherein said chitosan contains cross linked chitosan.

5. The solid substrate of claim 1, wherein said coral or coral derivative is aragonite, calcite, hydroxyapatite, mixtures thereof, or other polymorphs of the same.

6. The solid substrate of claim 1, wherein said first or second biocompatible polymer or a combination thereof further contains a cytokine, a growth factor, a chelator, a cell population, a therapeutic compound, a drug, or any combination thereof.

7. The solid substrate of claim 6, wherein said therapeutic compound or drug is an anti-inflammatory compound, an anti-infective compound, a pro-angiogenic factor or a combination thereof.

8. The solid substrate of claim 1, wherein said marine organism skeletal derivative is characterized by a specific fluid uptake capacity value of at least 75%, which specific fluid uptake capacity value is determined by establishing a spontaneous fluid uptake value divided by a total fluid uptake value, wherein said fluid is
(a) a protein-containing, salt-containing or carbohydrate containing solution;
(b) a biologic fluid that is autologous with respect to a cell or tissue of a subject when said solid substrate is contacted with a cell or tissue of said subject; or
(c) water.

9. The solid substrate of claim 1, wherein said marine organism skeletal derivative is characterized by having a contact angle value of less than 60 degrees, when in contact with a fluid, wherein said fluid is
(a) a protein-containing, salt-containing or carbohydrate containing solution;

(b) a biologic fluid that comprises cells or tissue; or (c) water.

10. A method of inducing or enhancing repair, regeneration or enhancement of formation of cartilage, bone or a combination thereof, said method comprising implanting in a subject, a solid substrate of claim 1 within a site in need of repair, regeneration or enhancement of formation of cartilage, bone or a combination thereof.

11. The method of claim 10, wherein said method comprises rendering said first phase more elastic following wetting of said first phase as a consequence of or during said implanting.

12. The method of claim 10, wherein a solid substrate comprising said second phase and said third phase of said three phases is implanted within said subject, and said first phase of said three phases is added to said solid substrate in situ.

13. The method of claim 10, wherein said method comprises positioning said solid substrate below the upper limit of said site such that said solid substrate does not protrude above an upper limit of said site.

14. The method of claim 10, wherein said subject is afflicted with a cartilage and/or bone defect or disorder or disease, wherein said cartilage defect or disorder comprises a full or partial thickness articular cartilage defect; osteochondral defect; a joint defect or a defect resulting from trauma, sports, repetitive stress or osteoarthritis.

15. The method of claim 10, wherein said solid substrate is positioned such that said second phase is implanted within or proximally to cartilage tissue and third porous phase is implanted within or proximally to bone tissue.

16. A kit for repair of cartilage comprising the solid substrate of claim 1; directions for utilizing said solid substrate in tissue repair; and optionally a tool for optimal insertion of said solid substrate, and a series of solid substrates of different sizes, shapes or a combination thereof.

17. A kit for repair of cartilage comprising a two phase solid substrate for use in making, in situ, a solid substrate that consists essentially of two phases and at least one biocompatible polymer; directions for utilizing said solid substrate in tissue repair; and optionally a tool for optimal insertion of said solid substrate, and a series of solid substrates of different sizes, shapes or a combination thereof, wherein said kit provides separately:

At least one biocompatible polymer and

A solid substrate having the first and second phases, the first phase consisting essentially of a marine organism skeletal derivative-based solid substrate that has a series of hollows along a longitudinal axis in said first phase; and the second phase consisting essentially of a marine organism skeletal derivative-based solid substrate that is a coral or coral derivative, wherein said coral or coral derivative is aragonite, calcite, hydroxyapatite, mixtures thereof, or other polymorphs of the same;

wherein the at least one biocompatible polymer comprises hyaluronic acid, sodium hyaluronate, or a cross linked hyaluronic acid or a combination thereof and wherein the kit is provided with instructions and appropriate tools for applying the at least one biocompatible polymer to said second phase of said solid substrate, in situ, such that some of the biocompatible polymer is located within the series of hollows in said first phase of said substrate and such that some of the biocompatible polymer creates a separate phase as a terminus of the two phase solid substrate.

* * * * *

UNITED STATES PATENT AND TRADEMARK OFFICE
CERTIFICATE OF CORRECTION

PATENT NO. : 10,271,938 B2
APPLICATION NO. : 14/390163
DATED : April 30, 2019
INVENTOR(S) : Altschuler It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 277 days.

Signed and Sealed this
Sixteenth Day of June, 2020

Andrei Iancu
*Director of the United States Patent and Trademark Office*